(12) United States Patent
Everett et al.

(10) Patent No.: US 10,534,003 B2
(45) Date of Patent: Jan. 14, 2020

(54) MULTI-PROTEIN BIOMARKER ASSAY FOR BRAIN INJURY DETECTION AND OUTCOME

(71) Applicant: THE JOHNS HOPKINS UNIVERSITY, Baltimore, MD (US)

(72) Inventors: Allen D. Everett, Glenwood, MD (US); Jennifer E. Van Eyk, Los Angeles, CA (US); Frederick Korley, Fulton, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/905,312

(22) PCT Filed: Jul. 17, 2014

(86) PCT No.: PCT/US2014/046986
§ 371 (c)(1),
(2) Date: Jan. 15, 2016

(87) PCT Pub. No.: WO2015/009907
PCT Pub. Date: Jan. 22, 2015

(65) Prior Publication Data
US 2016/0178643 A1 Jun. 23, 2016

Related U.S. Application Data

(60) Provisional application No. 61/847,213, filed on Jul. 17, 2013.

(51) Int. Cl.
| | | |
|---|---|---|
| C07K 16/18 | (2006.01) | |
| A61B 5/1477 | (2006.01) | |
| G01N 33/68 | (2006.01) | |
| C12Q 1/6883 | (2018.01) | |

(52) U.S. Cl.
CPC ....... *G01N 33/6893* (2013.01); *C12Q 1/6883* (2013.01); *C12Q 2600/158* (2013.01); *G01N 2333/4727* (2013.01); *G01N 2333/70525* (2013.01); *G01N 2333/825* (2013.01); *G01N 2333/988* (2013.01); *G01N 2800/28* (2013.01); *G01N 2800/2871* (2013.01)

(58) Field of Classification Search
None
See application file for complete search history.

(56) References Cited

U.S. PATENT DOCUMENTS

| | | |
|---|---|---|
| 6,780,606 B1 | 8/2004 | Jackowski |
| 6,884,591 B2 | 4/2005 | Janigro et al. |
| 7,144,708 B2 | 12/2006 | Janigro et al. |
| 7,396,654 B2 | 7/2008 | Hayes |
| 7,427,490 B2 | 9/2008 | Valkirs |
| 7,456,027 B2 | 11/2008 | Wang et al. |
| 8,460,888 B2 | 6/2013 | Lafaye et al. |
| 8,492,107 B2 | 7/2013 | Wang et al. |
| 8,557,526 B2 | 10/2013 | Ottens et al. |
| 8,663,911 B2 | 3/2014 | Vojdani |
| 9,194,867 B2 | 11/2015 | Vojdani |
| 2003/0077590 A1 | 4/2003 | Pedersen et al. |
| 2003/0224460 A1 | 12/2003 | Pedersen et al. |
| 2006/0257943 A1 | 11/2006 | Dambinova |
| 2007/0098728 A1 | 5/2007 | Pedersen et al. |
| 2008/0026485 A1 | 1/2008 | Hueber et al. |
| 2008/0131881 A1 | 6/2008 | Ladenson et al. |
| 2008/0220013 A1 | 9/2008 | Hochstrasser et al. |
| 2009/0068691 A1 | 3/2009 | Dave et al. |
| 2011/0082203 A1 | 4/2011 | Wang et al. |
| 2011/0207126 A1 | 8/2011 | Popko et al. |
| 2013/0252834 A1 | 9/2013 | Dayon et al. |
| 2014/0045713 A1 | 2/2014 | Everett et al. |
| 2014/0303041 A1 | 10/2014 | Hayes et al. |
| 2014/0342381 A1 | 11/2014 | Hayes |

(Continued)

FOREIGN PATENT DOCUMENTS

| | | |
|---|---|---|
| WO | 2003/016910 | 2/2003 |
| WO | 2003/059272 | 7/2003 |

(Continued)

OTHER PUBLICATIONS

Zetterberg et al., Brain Injury, 2009, 23(9):723-6.*
Wang et al (2008) MRI abnormalities of the brain in one-year-old children with sickle cell anemia. Pediatr Blood Cancer. Nov. 2008;51(5):643-6. doi: 10.1002/pbc.21612.
Pegelow et al (2008) Silent infarcts in children with sickle cell anemia and abnormal cerebral artery velocity. Arch Neurol. Dec. 2001;58(12):2017-21.
Vendt et al (2009) Silent Cerebral Infarct Transfusion (SIT) trial imaging core: application of novel imaging information technology for rapid and central review of MRI of the brain. J Digit Imaging. Jun. 2009;22(3):326-43. doi: 10.1007/s10278-008-9114-3. Epub Apr. 9, 2008.
Ottens et al (2006) Neuroproteomics in neurotrauma. Mass Spectrom Rev. May-Jun. 2006;25(3):380-408.

(Continued)

*Primary Examiner* — Olga N Chernyshev
(74) *Attorney, Agent, or Firm* — Melissa Hunter-Ensor; Leslie Serunian; Greenberg Traurig, LLP

(57) ABSTRACT

The present invention relates to the field of brain injuries. More specifically, the present invention provides methods and compositions useful in the diagnosis/prognosis/assessment of brain injuries. In a specific embodiment, a method for identifying which patients with traumatic brain injury (TBI) require a head computerized tomography (CT) scan for diagnosing acute intracranial pathology comprises the steps of (a) obtaining or collecting a sample from the patient; (b) measuring the levels of one or more biomarkers in the blood sample obtained from the patient, wherein the biomarkers comprise glial fibrillary acidic protein (GFAP), S100B, metallothionein 3 (MT3), neuron specific enolase (NSE) and intracellular adhesion molecule 5 (ICAM5); and (c) identifying the patient as requiring or not requiring a head CT scan based on the measured levels of one or more of biomarkers comprising GFAP, S100B, MT3, NSE and ICAM5.

7 Claims, 13 Drawing Sheets

(56) References Cited

U.S. PATENT DOCUMENTS

| | | |
|---|---|---|
| 2015/0118218 A1 | 4/2015 | Travis et al. |
| 2015/0119273 A1 | 4/2015 | Goldstein et al. |
| 2015/0141528 A1 | 5/2015 | Larner |
| 2015/0247867 A1 | 9/2015 | Curdt et al. |
| 2015/0268252 A1 | 9/2015 | Svetlov et al. |

FOREIGN PATENT DOCUMENTS

| | | |
|---|---|---|
| WO | 2004/059293 | 7/2004 |
| WO | 2006/012351 A2 | 2/2006 |
| WO | 2008/046509 A1 | 4/2008 |
| WO | 2009/143519 A2 | 11/2009 |
| WO | 2009143519 A2 | 11/2009 |
| WO | 2010/019553 A2 | 2/2010 |
| WO | 2010148391 A2 | 12/2010 |
| WO | 2011/032155 A2 | 3/2011 |
| WO | 2011-032155 A2 | 3/2011 |
| WO | 2012/155134 A2 | 11/2012 |
| WO | 2015066211 A1 | 5/2015 |

OTHER PUBLICATIONS

Berger et al (2006) The Use of Biomarkers After Inflicted Traumatic Brain Injury: Insight into Etiology, Pathophysiology, and Biochemistry. Clin Ped Emer Med 7(3):186-193.

Hergenroeder et al (2008) Biomarkers in the clinical diagnosis and management of traumatic brain injury. Mol Diagn Ther. 2008;12(6):345-58. doi: 10.2165/1250444-200812060-00002.

Zetterberg, H., et al., "Neurochemical aftermath of amateur boxing", Arch Neurol. (2006) vol. 63, pp. 1277-1280.

Laterza, O., et al., "Biomarkers of tissue injury", Biomarkers Med. (2008) vol. 2, No. 1, pp. 81-92.

Extended European Search Report dated Feb. 10, 2014 for EP application 11833480.

Savage, W., et al., "Glial fibrillary acidic protein as a plasma biomarker of brain injury in children with sickle cell disease", American Journal of Hematology (2011) vol. 86, No. 5.

Williams, L., et al., "Proteomic-based approach for biomarker discovery to predict silent cerebral infarct in patients with sickle cell disease" (2009) 51st annual meeting of the american society of hematology, New Orleans, LA.

Hoshi, T., et al., "Relations of serum high-sensitivity c-reactive protein and interleukin-6 levels with silent brain infarction", Stroke (2005) vol. 36, No. 4.

Ishigami, A., et al., "Abnormal accumulation of citrullinated proteins catalyzed by peptidylarginine deiminase in hippocampal extracts from patients with alzheimer's disease" Journal of Neuroscience Research (2005) vol. 80, pp. 120-128.

Oguz, K., et al., Assessment of citrullinated myelin by 1H-MR spectroscopy in early-onset multiple sclerosis Am. J. Neuroradiol (2009) vol. 30, pp. 716-721.

Thorsell, A., et al., "Neurogranin in cerebrospinal fluid as a marker of synaptic degeneration in Alzheimer's disease" Brain Research (2010) vol. 1362, pp. 13-22.

Pak, J., et al., "Involvement of neurogranin in the modulation of calcium/calmodulin-dependent protein kinase II, synaptic plasticity, and spatial learning: a study with knockout mice", Proc. Natl. Acad. Sci. USA, Oct. 10, 2000, vol. 97, No. 21, pp. 11232-11237.

NCBI GeneBank Accession No. NP_006167 (Jan. 14, 2011).

Tok, J., et al., "Single microbead SELEX for efficient ssDNA aptamer generation against botulinum neurotoxin", Chem. Commun., Mar. 18, 2008, pp. 1883-1885.

Watson, J., et al., "Localization of RC3 (neurogranin) in rat brain subcellular fractions", Molecular Brain Research, Dec. 1, 1994, vol. 27, No. 2, pp. 323-328.

Neuner-Jehle, M., et al., "Sleep deprivation differentially alters the mRNA and protein levels of neurogranin in rat brain", Brain Research, Jul. 1, 1995, vol. 685, No. 1-2, pp. 143-153.

Clayton, D., et al., "Conservation and expression of IQ-domain-containing calpacitin gene products (neuromodulin/GAP-43, neurogranin/RC3) in the adult and developing oscine song control system", Developmental Neurobiology, Feb. 1, 2009, vol. 69, No. 2-3, pp. 124-140.

Laterza, O., et al., "Identification of novel brain biomarkers", Clinical Chemistry, American Association for Clinical Chemistry, Washington, DC, Sep. 1, 2006, vol. 52, No. 9, pp. 1713-1721.

Hoehna, Y., et al., "Matrix metalloproteinase 9 regulates cell death following pilocarpine-induced seizures in the developing brain" Neurobiology of Disease (2012) vol. 48, pp. 339-347.

European Search Report dated Oct. 9, 2015 for EP application 13760865.

Zhang, H., et al., "Methods for peptide and protein quantitation by liquid chromatography—multiple reaction monitoring mass spectrometry" Molecular & Cellular Proteomics (2011) pp. 1-62.

European Search Report dated Jul. 13, 2015 for EP application 12782967.

Wu, L., et al., "Characterization, using comparative proteomics, of differentially expressed proteins in the hippocampus of the mesial temporal lobe of epileptic rats following treatment with valproate" Amino Acids (2011) vol. 40, pp. 221-238.

Iliuk, A., et al., "Aptamer in Bioanalytical applications" Analytical Chemistry (2011) vol. 83, pp. 4440-4452.

Tang, L., et al., "Attenuation of opioid tolerance by antisense oligodeoxynucleotides targeting neurogranin" European Journal of Pharmacology (2006) vol. 542, pp. 106-107.

Tang, L., et al., "Disruption of acute opioid dependence by antisense oligodeoxynucleotides targeting neurogranin" Brain Research (2007) vol. 1143, pp. 78-82.

Babcock, Lynn, "Ability of S100B to predict severity and cranial CT results in children with TBI," Brain Injury, Oct. 9, 2012, vol. 26, No. 11, pp. 1372-1380.

Berger et al., "Multiplex Assessment of Serum Biomarker Concentrations in Well-Appearing Children With Inflicted Traumatic Brain Injury," Pediatric Research, Jan. 1, 2009, vol. 65, No. 1, pp. 97-102.

Biberthaler et al., "Serum 5-100B Concentration Provides Additional Information for the Indiciation of Computer Tomography in Patients After Minor Head Injury," Shock, May 1, 2006, vol. 25, No. 5, pp. 446-453.

Ingerbrigtsen et al., "The Clinical Value of Serum S-100 Protein Measurements in Minor Head Injury: A Scandinavian Multicentre Study," Brain Injury, Dec. 1, 2000, vol. 14, No. 12, pp. 1047-1055.

Jeter et al., "Biomarkers for the Diagnosis and Prognosis of Mild Traumatic Brain Injury/Concussion," Journal of Neurotrauma, Apr. 15, 2014, vol. 30, No. 8, pp. 657-670.

Mondello et al., "Glial Neuronal Ratio: A Novel Index for Differentiating Injury Type in Patients with Severe Traumatic Brain Injury," Journal of Neurotraum, Apr. 10, 2012, vol. 29, No. 6, pp. 1096-1104.

Communication received from European Patent Office, for corresponding EP 148267867.7, dated Apr. 18, 2017 (20 pages).

Papa et al., "Elevated Levels of Serum Glial Fibrillary Acidic Protein Breakdown Products in ild and Moderate Traumatic Brain Injury Are Associated with Intracranial Lesions and Neurosurgical Intervention," Annals of Emergency Medicine, Jun. 1, 2012, vol. 59, No. 6, pp. 471-483.

Papa et al., "Serum levels of ubiquitin C-terminal hydrolase distinguish mild traumatic brain injury from trauma controls and are elevated in mild and moderate traumatic brain injury patients with intracranial lesions and neurosurgical intervention," Journal of Trauma and Acute Care Surgery, May 1, 2012, vol. 72, No. 5, pp. 1335-1344.

Rodrigues et al., "Increased serum brain derived neurotrophic factor (BDNF) following isolated severe traumatic brain injury in humans," Brain Injury, Taylor and Francis, London, GB, Jan. 1, 2008, vol. 22, No. Suppl. 1, p. 165.

Rostami et al.. "Proteomic-based identification of injury-specific patterns of biomarkers following different types of TBI," Abstracts of the Annual Meeting of the Soceity for Neuroscience, Society for Neuroscience, Jan. 1, 2010, vol. 40.

(56) References Cited

OTHER PUBLICATIONS

Rostami et al., "Alteration in BDNF and its receptors, full-length and truncated TrkB and p75NTR following penetrating traumatic brain injury," ScienceDirect, vol. 1542, pp. 195-205 (2014).
Griesbach, et al., "Alterations in BDNF and Synapsin I within the Occipital Cortex and Hippocampus after Mild Traumatic Brain Injury in the Developing Rat: Reflections of Injury-Induced Neuroplasticity," Journal of Neurotrauma, vol. 19, No. 7, pp. 803-814 (2002).
Koumura, A., et al., "Metallothionein-3 deficient mice exhibit abnormalities of psychological behaviors" Neuroscience Letters (2009) vol. 467, pp. 11-14.
Lange, R., et al., "Evaluation of eight plasma proteins as candidate blood-based biomarkers for malignant gliomas" Cancer Investigation (2014) vol. 32, pp. 423-429.
Oliveira, C., et al., "Outcome biomarkers following severe traumatic brain injury" Rev Bras Ter Intensiva (2008) vol. 20, No. 4, pp. 411-421.
Radka, S., et al., "Presence of brain-derived neurotrophic factor in brain and human and rat but not mouse serum detected by a sensitive and specific immunoassay" Brain Research (1996) vol. 709, pp. 122-130.
Zetterberg, H., "Biomarkers of mild traumatic brain injury in cerebrospinal fluid and blood" Focus on Traumatic Brain Injury (2013) vol. 9, pp. 201-210.
Haqqani et al (2007) Biomarkers and diagnosis; protein biomarkers in serum of pediatric patients with severe traumatic brain injury identified by ICAT-LC-MS/MS. J Neurotrauma. Jan. 2007;24(1):54-74.
Ishigami et al., "Abnormal accumulation of citrullinated proteins catalyzed by peptidylarginine deiminase in hippocampal extracts from patients with Alzheimer's disease", Journal of Neuroscience Research. vol. 80, Issue 1, pp. 120-128 (Apr. 1, 2005).
Oguz et al., "Assessment of citrullinated myelin by 1H-MR spectroscopy in early-onset multiple sclerosis", American Journal of Neuroradiology, vol. 30, No. 4, pp. 716-721 (Jan. 15, 2009).
Examination Report received in European Patent Office in corresponding European Patent Application No. 14826786.7 dated Apr. 6, 2018 (5 pages).
English translation of Office Action in corresponding Japanese Patent Application No. 2016-527092, dated Jul. 26, 2018 (3 pages).
Feala et al., "Systems Biology Approaches for Discovering Biomarkers for Traumatic Brain Injury", Journal of Neurotrauma, vol. 30, No. 13, pp. 1101-1116 (2013).
Zhang et al., "Human traumatic Brain Injury Induces Autoantibody Response Against Glial Fibrillary Acidic Protein and Its Breakdown Products", PLoS One, vol. 9, Issue 3, e92698 (internal pp. 1-16) (2014).
Translation of Second Office Action received in corresponding Japanese application No. P2016-527092, dated Feb. 6, 2019, (2 pages).
Buki et al., "Minor and Repetitive Head Injury", Advances and Technical Standards in Neurosurgery 42, 2015, pp. 147-192, Springer International Publishing Switzerland.
Ichkova et al., "New Biomarker Stars for Traumatic Brain Injury", Journal of Cerebral Blood Flow & Metabolism, 2017, vol. 37(10), 3276-3277.
Ke et al., "Increased Expression of Small Heat Shock Protein αB-Crystallin After Intracerebral Hemorrhage in Adult Rats", J. Mol. Neurosci, 2013, 51:159-169, Springer Science+Business Media New York.
Lumpkins et al., "Glial Fibrillary Acidic Protein is Highly Correlated with Brain Injury", The Journal of Trauma, 2008, 65, pp. 778-784.
Martinez et al., "Type-Dependent Oxidative Damage in Frontotemporal Lobar Degeneration: Cortical Astrocytes are Targets of Oxidative Damage", j Neuropathol Exp Neurol, vol. 67, No. 12, Dec. 2008, pp. 1122-1136.
McMahon et al., "Measurement of the Glial Fibrillary Acidic protein and its Breakdown Products GFAP-BDP Biomarker for the Detection of Traumatic Brain Injury Compared to Computed Tomography and Magnetic Resonance Imaging", Journal of Neurotrauma, 35:527-533, Apr. 15, 2015.
Newcombe et al., "Distribution of Glial Fibrillary Acidic Protein in Gliosed Human White Matter", Journal of Neurochemistry, 47, 1986, pp. 1713-1719.
Okonkwo et al., "GFAP-BDP as an Acute Diagnostic Marker in Traumatic Brain Injury: Results from the Prospective Transforming Research and Clinical Knowledge in Traumatic Brain Injury Study", Journal of Neurotrauma, 30:1490-1497, Sep. 1, 2013.
Pelinka et al., "Glial Fibrillary Acidic Protein in Serum After Traumatic Brain Injury and Multiple Trauma", The Journal of Trauma, 2004, 57:1006-1012.
Pelinka et al., "GFAP Versus S100B in Serum after Traumatic Brain Injury: Relationship to Brain Bamage and Outcome", Journal of Neurotrauma, vol. 21, No. 11, 2004, pp. 1553-1561.
Rohn et al., "Caspase-Cleaved Glial Fibrillary Acidic Protein within Cerebellar White Matter of the Alzheimer's Disease Brain", Int J Clin Pathol, 2013, 6(1), pp. 41-48.
Shen et al., "Addressing the Needs of Traumatic Brain Injury with Clinical Proteomics", Clinical Proteomics, 2014, 11:11, (13 pages).
Vasquez et al., "Creatine Kinase BB and Neuron-Specific Enolase in Cerebrospinal Fluid in the Diagnosis of Brain Insult", The American Journal of Forensic Medicine and Pathology, 16(3), pp. 210-214, 1995.
Yang et al., "Glial Fibrillary Acidic Protein: from Intermediate Filament Assembly and Gliosis to Neurobiomarker", Trends in Neuroscience, Jun. 2015, vol. 38, No. 6, pp. 364-374.
Zoltewicz et al., "Characterization of Antibodies that Detect Human GFAP after Traumatic Brain Injury", Biomarker Insights, 2012:7, pp. 71-79.
Office Action, dated Jan. 14, 2019, received in corresponding European Patent Application No. 14826786.7, (8 pages).
English translation of Office Action, dated Mar. 11, 2019, received in corresponding Israel Patent Application No. 243393, (2 pages).

* cited by examiner

MULTI-PROTEIN BIOMARKER ASSAY FOR BRAIN INJURY DETECTION AND OUTCOME

CROSS-REFERENCE TO RELATED APPLICATIONS

This application is a 35 U.S.C. § 371 U.S. national entry of International Application PCT/US2014/046986, having an international filing date of Jul. 17, 2014, which claims the benefit of U.S. Provisional Application No. 61/847,213, filed Jul. 17, 2013, the content of each of the aforementioned applications is herein incorporated by reference in their entirety.

FIELD OF THE INVENTION

The present invention relates to the field of brain injuries. More specifically, the present invention provides methods and compositions useful in the diagnosis/prognosis/assessment of brain injuries.

BACKGROUND OF THE INVENTION

Clinical tools such as physical exam, and central nervous system (CNS) imaging (computerized tomography (CT) scan or magnetic resonance imaging (MRI)) are subjective, not widely available, not sensitive or specific enough and too costly to identify all patients with CNS injury and therefore has a high false negative rate. This can include individuals on life support or cardiopulmonary bypass, trauma, loss of oxygen, etc. regardless of the initial injury or disease. There is a great clinical need to identify patients with CNS or brain injury because such individuals are at significant risk of progressing to overt stroke, development of cognitive and motor loss, dementia and poor mental performance. In addition, accurate and sensitive identification of CNS injury by circulating biomarkers will provide an objective gold standard to test and compare new therapeutic modalities for efficacy.

SUMMARY OF THE INVENTION

The present invention is based, at least in part, on the discovery that the biomarkers GFAP (glial fibrillary acidic protein), S100B, MT3 (metallothionein 3), NSE (neuron specific enolase) and ICAM5 (intracellular adhesion molecule 5) (and/or any of their post-translational modified forms or their isoforms) in combination can discriminate which patients with traumatic brain injury (TBI) require a head CT scan to rule out intracranial hemorrhage versus concussion alone. If implemented as an initial response (e.g., in the emergency department (ED) setting) or later (e.g., neurology department), the present invention would decrease head CT scan utilization, decreasing health care costs and radiation exposure.

Accordingly, in certain embodiments, blood levels of GFAP, S100B, MT3, ICAM5, BDNF, and/or NSE in combination on arrival in the Emergency Department (ED) can predict the need for a head CT scan in patients presenting within 24 hours of TBI. Sensitivity is higher with the markers in combination than any of them alone. In addition, these makers in combination can potentially be used any time when injury occurs (e.g., time of injury, in ambulance, emergency department, or hospital unit).

In a specific embodiment, a method for identifying which patients with traumatic brain injury (TBI) require a head computerized tomography (CT) scan for diagnosing acute intracranial pathology comprises the steps of (a) contacting a biological sample obtained from the patient with a plurality of binding agents that selectively bind to a plurality of biomarkers for a period of time sufficient to form binding agent-biomarker complexes, wherein the plurality of biomarkers comprises one or more of glial fibrillary acidic protein (GFAP), S100B, metallothionein 3 (MT3), neuron specific enolase (NSE) and intracellular adhesion molecule 5 (ICAM5); (b) detecting the binding agent-biomarker complexes, thereby determining the levels of expression of the biomarkers in the biological sample; and (c) comparing the levels of expression of the plurality of biomarkers in the biological sample with predetermined threshold values, wherein levels of expression of at least one of the plurality of biomarkers above or below the predetermined threshold values indicates the necessity of a head CT scan.

In another embodiment, a method for identifying which patients with traumatic brain injury (TBI) require a head CT scan for diagnosing acute intracranial pathology comprises the steps of (a) contacting a biological sample obtained from the subject with a composition comprising a solid substrate and a plurality of binding agents immobilized on the substrate, wherein each of the binding agents is immobilized at a different, indexable, location on the substrate and the binding agents specifically bind to a plurality of biomarkers, wherein the plurality of polypeptide biomarkers comprises one or more of GFAP, S100B, MT3, NSE, and ICAM5; (b) detecting binding of the plurality of binding agents to the plurality of biomarkers, thereby determining the levels of expression of the plurality of biomarkers in the biological sample; and (c) comparing the levels of expression of the plurality of biomarkers in the biological sample with predetermined threshold values, wherein levels of expression of at least one of the plurality of biomarkers above or below the predetermined threshold values indicates the necessity of a head CT scan.

The present invention also provides methods for method for diagnosing a patient with TBI as likely having intracranial hemorrhage (ICH) comprising the steps of (a) contacting a biological sample obtained from the patient with a plurality of binding agents that selectively bind to a plurality of biomarkers for a period of time sufficient to form binding agent-biomarker complexes, wherein the plurality of biomarkers comprises one or more of GFAP, S100B, MT3, NSE, and ICAM5; (b) detecting the binding agent-biomarker complexes, thereby determining the levels of expression of the biomarkers in the biological sample; and (c) comparing the levels of expression of the plurality of biomarkers in the biological sample with predetermined threshold values, wherein levels of expression of at least one of the plurality of biomarkers above or below the predetermined threshold values indicates the patient likely has ICH.

In yet another embodiment, a method for diagnosing a patient with TBI as likely having ICH comprises the steps of (a) contacting a biological sample obtained from the subject with a composition comprising a solid substrate and a plurality of binding agents immobilized on the substrate, wherein each of the binding agents is immobilized at a different, indexable, location on the substrate and the binding agents specifically bind to a plurality of biomarkers, wherein the plurality of polypeptide biomarkers comprises one or more of GFAP, S100B, MT3, NSE, and ICAM5; (b) detecting binding of the plurality of binding agents to the plurality of biomarkers, thereby determining the levels of expression of the plurality of biomarkers in the biological sample; and (c) comparing the levels of expression of the plurality of biomarkers in the biological sample with predetermined threshold values, wherein levels of expression of at least one of the plurality of biomarkers above or below the predetermined threshold values indicates the patient likely has ICH.

In certain embodiments, the plurality of biomarkers comprises GFAP and S100B; GFAP and MT3; GFAP and NSE; GFAP, ICAM and S100B; GFAP, ICAM5 and MT3; GFAP, MT3 and S100B; GFAP, NSE and S100B; or GFAP, ICAM5, MT3 and S100B. In more specific embodiments, the predetermined threshold values for the biomarkers comprise GFAP>0.04 ng/ml, ICAM>17 ng/ml, S100B>2 ng/ml, MT3>0.95 ng/ml, and NSE<71 ng/ml. In particular embodiments, the biological sample is selected from the group consisting of blood, plasma, serum or cerebrospinal fluid (CSF). In other embodiments, the binding agents comprise antibodies or antigen-binding fragments thereof.

The present invention also provides compositions comprising a solid substrate and a plurality of binding agents. In one embodiment, a composition comprises a solid substrate and a plurality of binding agents immobilized on the substrate, wherein each of the binding agents immobilized at a different, indexable location on the substrate and the binding agents specifically bind to a plurality of biomarkers, wherein the plurality of biomarkers comprise GFAP, S100B, MT3, NSE, and ICAM5. In a further embodiment, the plurality of biomarkers further comprises brain-derived neurotrophic factor (BDNF). In particular embodiments, the binding agents are labeled with a detectable moiety. The dateable moiety can be selected from the group consisting of luminescent agents, chemiluminescent agents, radioisotopes, colorimetric agents; and enzyme-substrate agents. In certain embodiments, the binding agents comprise antibodies or antigen-binding fragments thereof.

In yet another embodiment, a method for identifying which patients with traumatic brain injury (TBI) require a head computerized tomography (CT) scan for diagnosing acute intracranial pathology comprises the steps of (a) obtaining or collecting a sample from the patient; (b) measuring the levels of one or more biomarkers in the blood sample obtained from the patient, wherein the biomarkers comprise glial fibrillary acidic protein (GFAP), S100B, metallothionein 3 (MT3), neuron specific enolase (NSE) and intracellular adhesion molecule 5 (ICAM5); and (c) identifying the patient as requiring or not requiring a head CT scan based on the measured levels of one or more of biomarkers comprising GFAP, S100B, MT3, NSE and ICAM5. The biomarkers can further comprise BDNF. The sample can be any appropriate biological sample including blood and other liquid samples of biological origin including, but not limited to, peripheral blood, serum, plasma, cerebrospinal fluid, urine, saliva, stool and synovial fluid. In a specific embodiment, the sample is blood. In an alternative embodiment, the sample is serum. In another specific embodiment, the sample is CSF.

In particular embodiments, variants of the biomarkers can be used including protein splice variants (isoforms), polymorphisms, degraded and other post-translational modified forms including citrullinations, glycosylations, acetylations, phosphorylations and the like. In certain embodiments, the measuring step can comprise measuring modified and unmodified forms of the biomarkers. Analysis of the amounts or ratios of the amounts can be used in the identification step. More specifically, in certain embodiments, the measuring step can be performed using an enzyme linked immunosorbent assay (ELISA). In other embodiments, mass spectrometry is used. In certain embodiments, a logistic regression model is used in the identification step.

In other embodiments, the one or more biomarkers comprise GFAP and S100B, GFAP and MT3, GFAP and NSE, GFAP and ICAM and S100B, GFAP and ICAM5 and MT3, GFAP and MT3 and S100B, GFAP and NSE and S100B, and GFAP and ICAM5 and MT3 and S100B. In more specific embodiments, the cutoff values for the biomarkers comprise GFAP>0.04 ng/ml, ICAM>17 ng/ml, S100B>2 ng/ml, MT3>0.95 ng/ml, and NSE<71 ng/ml.

In another specific embodiment of the present invention, a method for diagnosing a patient with TBI as likely having intracranial hemorrhage (ICH) comprises the steps of (a) obtaining a blood sample from the patient; (b) measuring the levels of one or more biomarkers in the blood sample obtained from the patient using an ELISA, wherein the biomarkers comprise GFAP, S100B, MT3, NSE and ICAM5; and (c) identifying the patient as likely having ICH based on the measured levels of one or more of biomarkers comprising GFAP, S100B, MT3, NSE and ICAM5. The method can further comprise the step of performing a head CT scan to confirm ICH diagnosis. In particular embodiments, the one or more biomarkers comprise GFAP and S100B, GFAP and MT3, GFAP and NSE, GFAP and ICAM and S100B, GFAP and ICAM5 and MT3, GFAP and MT3 and S100B, GFAP and NSE and S100B, and GFAP and ICAM5 and MT3 and S100B. In certain embodiments, the cutoff values for the biomarkers comprise GFAP>0.04 ng/ml, ICAM>17 ng/ml, S100B>2 ng/ml, MT3>0.95 ng/ml, and NSE<71 ng/ml. In specific embodiments, a logistic regression model is used in the identification step.

The present invention is also based on the discovery that circulating brain derived neurotrophic factor (BDNF, and or its processed or post-translational modified forms and variants) concentration in blood (serum/plasma and potentially other body fluid) alone and even more significantly in combination with GFAP (and/or its modified variants) can differentiate between patients with and those without traumatic brain injury and can predict short term (weeks) neurologic outcomes, return to work and as an indicator of intervention success.

In other embodiments, blood levels of BDNF decrease in ED patients with TBI, making it a biomarker of concussive brain injury. This marker can be used any time when injury occurs (e.g., at the time of injury, in ambulance, emergency department or hospital unit). In further embodiments, blood levels of BDNF in combination with GFAP predict post-concussive symptoms and disability.

In another aspect, the present invention provides methods for identifying a patient as having TBI. In a specific embodiment, the method comprises (a) contacting a biological sample obtained from the patient with a binding agent that selectively binds to BDNF for a period of time sufficient to form binding agent-BDNF complex; (b) detecting the binding agent-BDNF complex, thereby measuring the level of expression of BDNF in the biological sample; and (c) identifying the patient has having TBI based on the measured level of BDNF as compared to a control. In a more specific embodiment, an area under the receiver operator characteristic curve analysis is used to identify the patient as having TBI. In another embodiment, a logistic regression model is used to identify the patient as having TBI.

In another embodiments, a method for diagnosing a patient as having TBI comprises the steps of (a) contacting a biological sample obtained from the patient with a composition comprising a solid substrate and a plurality of binding agents immobilized on the substrate, wherein each of the binding agents is immobilized at a different, indexable, location on the substrate and the binding agents specifically bind to a plurality of biomarkers, wherein the plurality of polypeptide biomarkers comprises BDNF and one or more of neurogranin (NRGN), myelin basic protein (MBP), PAD-2, tubulin beta-4B chain, tubulin alpha-1B chain, CNPase, PPIA, Septin-7, Elongation factor1-alpha2, TPPP, TPPP3, Ermin Isoform 2, NDRG2 Isoform 2, astrotactin 1 (ASTN1), brain angiogenesis inhibitor 3 (BAI3); carnosine dipeptidase 1 (CNDP1); ERMIN; glutamate receptor metabotropic 3 (GRM3); kelch-like protein 32 (KLH32); melanoma antigen family E,2 (MAGE2); neuregulin 3 (NRG3); oligodendrocyte myelin glycoprotein (OMG); solute carrier family 39 (zinc transporter); reticulon 1 (RTN1); and peptidylarginine deiminase (types 1-4 and 6) (PAD); (b) detecting binding of the plurality of binding agents to the plurality of biomarkers, thereby determining the levels of expression of the plurality of biomarkers in the biological sample; and (c) comparing the levels of expression of the plurality of biomarkers in the biological sample with predetermined threshold values, wherein levels of expression of at least one of the plurality of biomarkers above or below the predetermined threshold values indicates the patient has TBI.

In yet another embodiment, a method for diagnosing TBI in a patient comprising the steps of (a) collecting a sample from the patient; (b) measuring the levels of a panel biomarkers in the sample collected from the patient using mass spectrometry or ELISA, wherein the panel of biomarkers comprises BDNF, isoforms thereof, post-translationally modified forms thereof, or combinations of any of the foregoing; and (c) comparing the levels of the panel of biomarkers with predefined levels of the same panel of biomarkers that correlate to a patient having TBI and predefined levels of the same panel of biomarkers that correlate to a patient not having TBI, wherein a correlation to one of the predefined levels provides the diagnosis. The present invention also provides a method for predicting short and long-term post-concussive symptoms and disability after TBI in a patient comprising the steps of (a) collecting a sample from the patient; (b) measuring the levels of a panel biomarkers in the sample collected from the patient using mass spectrometry or ELISA, wherein the panel of biomarkers comprises and BDNF, isoforms thereof, post-translationally modified forms thereof, or combinations of any of the foregoing; and (c) comparing the levels of the panel of biomarkers with predefined levels of the same panel of biomarkers that correlate to a patient having persistent post-concussive symptoms, predefined levels of the same panel of biomarkers that correlate to a patient having disability, predefined levels of the same panel of biomarkers that correlate to a patient not having post-concussive symptoms, and predefined levels of the same panel of biomarkers that correlate to a patient not having disability, wherein a correlation to one of the predefined levels provides the diagnosis.

In a specific embodiment, a method for diagnosing TBI in a patient comprises the steps of (a) collecting a sample from the patient; (b) measuring the levels of a panel biomarkers in the sample collected from the patient using mass spectrometry or ELISA, wherein the panel of biomarkers comprises brain derived neurotrophic factor (BDNF), isoforms thereof, post-translationally modified forms thereof, or combinations of any of the foregoing; and (c) comparing the levels of the panel of biomarkers with predefined levels of the same panel of biomarkers that correlate to a patient having TBI and predefined levels of the same panel of biomarkers that correlate to a patient not having TBI, wherein a correlation to one of the predefined levels provides the diagnosis.

The present invention also provides a method for predicting short and long-term post-concussive symptoms and disability after TBI in a patient comprising the steps of (a) collecting a sample from the patient; (b) measuring the levels of a panel biomarkers in the sample collected from the patient using mass spectrometry or ELISA, wherein the panel of biomarkers comprises GFAP and BDNF, isoforms thereof, post-translationally modified forms thereof, or combinations of any of the foregoing; and (c) comparing the levels of the panel of biomarkers with predefined levels of the same panel of biomarkers that correlate to a patient having persistent post-concussive symptoms, predefined levels of the same panel of biomarkers that correlate to a patient having disability, predefined levels of the same panel of biomarkers that correlate to a patient not having post-concussive symptoms, and predefined levels of the same panel of biomarkers that correlate to a patient not having disability, wherein a correlation to one of the predefined levels provides the diagnosis.

In another aspect, the present invention also provides kits. In one embodiment, a kit comprises means for measuring the levels of one or more human biomarkers comprising GFAP, S100B, MT3, NSE, ICAM5 and BDNF, isoforms thereof, post-translationally modified forms thereof, or combinations of any of the foregoing. In certain embodiments, the kit comprises antibodies for performing an immunoassay to measure biomarker levels. In other embodiments, aptamers are used. In a further embodiment, the kit comprises a substrate for collecting a sample from the patient.

In yet another embodiment, the present invention provides a kit comprising (a) a plurality of biomarker binding agents capable of specifically binding to a plurality of biomarkers within a biological sample from a human patient suspected of having traumatic brain injury, wherein the biomarkers comprise GFAP, S100B, MT3, NSE, ICAM5 and BDNF; and (b) a detecting reagent or a detecting apparatus capable of indicating binding of the binding agents to one or more biomarkers.

DETAILED DESCRIPTION OF THE INVENTION

Figure 1:
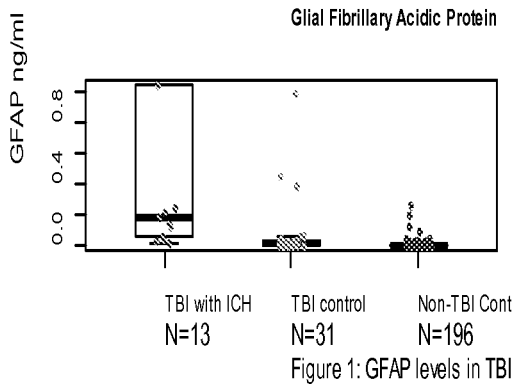
FIG. 1. GFAP levels in TBI cases and controls.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies.

As used herein, the term "antigen" is generally used in reference to any substance that is capable of reacting with an antibody. More specifically, as used herein, the term "antigen" refers to a synthetic peptide, polypeptide, protein or fragment of a polypeptide or protein, or other molecule which elicits an antibody response in a subject, or is recognized and bound by an antibody.

As used herein, the term "biomarker" refers to a molecule that is associated either quantitatively or qualitatively with a biological change. Examples of biomarkers include polypeptides, proteins or fragments of a polypeptide or protein; and polynucleotides, such as a gene product, RNA or RNA fragment; and other body metabolites. In certain embodiments, a "biomarker" means a compound that is differentially present (i.e., increased or decreased) in a biological sample from a subject or a group of subjects having a first phenotype (e.g., having a disease or condition) as compared to a biological sample from a subject or group of subjects having a second phenotype (e.g., not having the disease or condition or having a less severe version of the disease or condition). A biomarker may be differentially present at any level, but is generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (e.g., a p-value less than 0.05 and/or a q-value of less than 0.10 as determined using, for example, either Welch's T-test or Wilcoxon's rank-sum Test).

The term "brain injury" refers to a condition in which the brain is damaged by injury caused by an event. As used herein, an "injury" is an alteration in cellular or molecular integrity, activity, level, robustness, state, or other alteration that is traceable to an event. For example, an injury includes a physical, mechanical, chemical, biological, functional, infectious, or other modulator of cellular or molecular characteristics. An event can include a physical trauma such as a single or repetitive impact (percussive) or a biological abnormality such as a stroke resulting from either blockade or leakage of a blood vessel. An event is optionally an infection by an infectious agent. A person of skill in the art recognizes numerous equivalent events that are encompassed by the terms injury or event.

More specifically, the term "brain injury" refers to a condition that results in central nervous system damage, irrespective of its pathophysiological basis. Among the most frequent origins of a "brain injury" are stroke and traumatic brain injury (TBI). A "stroke" is classified into hemorrhagic and non-hemorrhagic. Examples of hemorrhagic stroke include cerebral hemorrhage, subarachnoid hemorrhage, and intracranial hemorrhage secondary to cerebral arterial malformation, while examples of non-hemorrhagic stroke include cerebral infarction.

The term "traumatic brain injury" or "TBI" refer to traumatic injuries to the brain which occur when physical trauma causes brain damage. For example, TBI can result from a closed head injury or a penetrating head injury. A "non-traumatic brain injury" refers to brain injuries that do not involve ischemia or external mechanical force (e.g., stroke, Alzheimer's disease, Parkinson's disease, Huntington's disease, multiple sclerosis, amyotrophic lateral sclerosis, brain hemorrhage, brain infections, brain tumor, among others).

The term "brain injury" also refers to subclinical brain injury, spinal cord injury, and anoxic-ischemic brain injury. The term "subclinical brain injury" (SCI) refers to brain injury without overt clinical evidence of brain injury. A lack of clinical evidence of brain injury when brain injury actually exists could result from degree of injury, type of injury, level of consciousness, medications particularly sedation and anesthesia.

The "spinal cord injury" refers to a condition in which the spinal cord receives compression/detrition due to a vertebral fracture or dislocation to cause dysfunction. As used herein, the term "anoxic-ischemic brain injury" refers to deprivation of oxygen supply to brain tissue resulting in compromised brain function and includes cerebral hypoxia. For example, anoxic-ischemic brain injury includes focal cerebral ischemia, global cerebral ischemia, hypoxic hypoxia (i.e., limited oxygen in the environment causes reduced brain function, such as with divers, aviators, mountain climbers, and fire fighters, all of whom are at risk for this kind of cerebral hypoxia), obstructions in the lungs (e.g., hypoxia resulting from choking, strangulation, the crushing of the windpipe).

The term "brain injury biomarker" (BIB), "brain injury biomarker protein", "brain injury biomarker peptide", brain injury biomarker polypeptide" and the like refer to a protein, including those described herein, that can be used in a method of the present invention, e.g., to diagnose brain injury in a patient. Brain injury biomarker proteins include, but are not limited to, GFAP, S100B, MT3, ICAM5, BDNF, and/or NSE. The term also includes other brain injury biomarker proteins known in the art including neurogranin (NRGN), myelin basic protein (MBP), PAD-2, tubulin beta-4B chain, tubulin alpha-1B chain, CNPase, PPIA, Septin-7, Elongation factor1-alpha2, TPPP, TPPP3, Ermin Isoform 2, NDRG2 Isoform 2, astrotactin 1 (ASTN1), brain angiogenesis inhibitor 3 (BAI3); carnosine dipeptidase 1 (CNDP1); ERMIN; glutamate receptor metabotropic 3 (GRM3); kelch-like protein 32 (KLH32); melanoma antigen family E,2 (MAGE2); neuregulin 3 (NRG3); oligodendrocyte myelin glycoprotein (OMG); solute carrier family 39 (zinc transporter); reticulon 1 (RTN1); and peptidylarginine deiminase (types 1-4 and 6) (PAD).

In addition, the term "brain injury biomarkers" also includes the isoforms and/or post-translationally modified forms of any of the foregoing. The present invention contemplates the detection, measurement, quantification, determination and the like of both unmodified and modifided (e.g., citrullination or other post-translational modification) proteins/polypeptides/peptides as well as autoantibodies to any of the foregoing. In certain embodiments, it is understood that reference to the detection, measurement, determination, and the like, of a biomarker refers detection of the protein/polypeptide/peptide (modified and/or unmodified). In other embodiments, reference to the detection, measurement, determination, and the like, of a biomarker refers detection of autoantibodies of the protein/polypeptide/peptide.

As used herein, the terms "comparing" or "comparison" refers to making an assessment of how the proportion, level or cellular localization of one or more biomarkers in a sample from a patient relates to the proportion, level or cellular localization of the corresponding one or more biomarkers in a standard or control sample. For example, "comparing" may refer to assessing whether the proportion, level, or cellular localization of one or more biomarkers in a sample from a patient is the same as, more or less than, or different from the proportion, level, or cellular localization of the corresponding one or more biomarkers in standard or control sample. More specifically, the term may refer to assessing whether the proportion, level, or cellular localization of one or more biomarkers in a sample from a patient is the same as, more or less than, different from or otherwise corresponds (or not) to the proportion, level, or cellular localization of predefined biomarker levels/ratios that correspond to, for example, a patient having brain injury, not having brain injury, is responding to treatment for brain injury, is not responding to treatment for brain injury, is/is not likely to respond to a particular brain injury treatment, or having/not having another disease or condition. In a specific embodiment, the term "comparing" refers to assessing whether the level of one or more biomarkers of the present invention in a sample from a patient is the same as, more or less than, different from other otherwise correspond (or not) to levels/ratios of the same biomarkers in a control sample (e.g., predefined levels/ratios that correlate to uninfected individuals, standard brain injury levels/ratios, etc.).

In another embodiment, the terms "comparing" or "comparison" refers to making an assessment of how the proportion, level or cellular localization of one or more biomarkers in a sample from a patient relates to the proportion, level or cellular localization of another biomarker in the same sample. For example, a ratio of one biomarker to another from the same patient sample can be compared. In another embodiment, a level of one biomarker in a sample (e.g., a post-translationally modified biomarker protein) can be compared to the level of the same biomarker (e.g., unmodified biomarker protein) in the sample. Ratios of modified: unmodified biomarker proteins can be compared to other protein ratios in the same sample or to predefined reference or control ratios.

As used herein, the terms "indicates" or "correlates" (or "indicating" or "correlating," or "indication" or "correlation," depending on the context) in reference to a parameter, e.g., a modulated proportion, level, or cellular localization in a sample from a patient, may mean that the patient has a brain injury or is otherwise suffering from neurodegeneration. In specific embodiments, the parameter may comprise the level of one or more biomarkers of the present invention. A particular set or pattern of the amounts of one or more biomarkers may indicate that a patient has a brain injury (i.e., correlates to a patient having brain injury). In other embodiments, a correlation could be the ratio of a post-translationally modified protein to the unmodified protein indicates (or a change in the ratio over time or as compared to a reference/control ratio) could mean that the patient has a brain injury).

In other embodiments, a particular set or pattern of the amounts of one or more biomarkers may be correlated to a patient being unaffected (i.e., indicates a patient does not have brain injury). In certain embodiments, "indicating," or "correlating," as used according to the present invention, may be by any linear or non-linear method of quantifying the relationship between levels/ratios of biomarkers to a standard, control or comparative value for the assessment of the diagnosis, prediction of brain injury or brain injury progression, assessment of efficacy of clinical treatment, identification of a patient that may respond to a particular treatment regime or pharmaceutical agent, monitoring of the progress of treatment, and in the context of a screening assay, for the identification of an anti-brain injury therapeutic.

The terms "patient," "individual," or "subject" are used interchangeably herein, and refer to a mammal, particularly, a human. The patient may have a mild, intermediate or severe disease or condition. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining or providing a patient sample and/or detecting the level of a biomarker(s) in a sample. In one embodiment, the terms refer to obtaining or providing a patient sample and detecting the level of one or more biomarkers in the sample. In another embodiment, the terms "measuring" and "determining" mean detecting the level of one or more biomarkers in a patient sample. The term "measuring" is also used interchangeably throughout with the term "detecting." In certain embodiments, the term is also used interchangeably with the term "quantitating."

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of brain injury. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, cord blood, amniotic fluid, cerebrospinal fluid, urine, saliva, stool and synovial fluid), solid tissue samples such as a biopsy specimen or tissue cultures or cells derived therefrom and the progeny thereof. In certain embodiment, a sample comprises cerebrospinal fluid. In a specific embodiment, a sample comprises a blood sample. In another embodiment, a sample comprises a plasma sample. In yet another embodiment, a serum sample is used.

The definition of "sample" also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

Various methodologies of the instant invention include a step that involves comparing a value, level, feature, characteristic, property, etc. to a "suitable control," referred to interchangeably herein as an "appropriate control," a "control sample," a "reference" or simply a "control." A "suitable control," "appropriate control," "control sample," "reference" or a "control" is any control or standard familiar to one of ordinary skill in the art useful for comparison purposes. A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype. For example, a "brain injury-positive reference level" of a biomarker means a level of a biomarker that is indicative of a positive diagnosis of brain injury in a subject, and a "brain injury-negative reference level" of a biomarker means a level of a biomarker that is indicative of a negative diagnosis of brain injury in a subject. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). Such reference levels may also be tailored to specific techniques that are used to measure levels of biomarkers in biological samples (e.g., LC-MS, GC-MS, ELISA, PCR, etc.), where the levels of biomarkers may differ based on the specific technique that is used.

In one embodiment, a "suitable control" or "appropriate control" is a value, level, feature, characteristic, property, etc., determined in a cell, organ, or patient, e.g., a control or normal cell, organ, or patient, exhibiting, for example, normal traits. For example, the biomarkers of the present invention may be assayed for levels/ratios in a sample from an unaffected individual (UI) or a normal control individual (NC) (both terms are used interchangeably herein). For example, a "suitable control" or "appropriate control" can be a value, level, feature, characteristic, property, ratio, etc. determined prior to performing a therapy (e.g., brain injury treatment) on a patient or a value, level, feature, characteristic, property, ratio, etc. determined prior to injury (e.g., a baseline test). In yet another embodiment, a transcription rate, mRNA level, translation rate, protein level/ratio, biological activity, cellular characteristic or property, genotype, phenotype, etc., can be determined prior to, during, or after administering a therapy into a cell, organ, or patient. In a further embodiment, a "suitable control" or "appropriate control" is a predefined value, level, feature, characteristic, property, ratio, etc. A "suitable control" can be a profile or pattern of levels/ratios of one or more biomarkers of the present invention that correlates to brain injury, to which a patient sample can be compared. The patient sample can also be compared to a negative control, i.e., a profile that correlates to not having brain injury.

As used herein, the term "predetermined threshold value of expression" of a biomarker refers to the level of expression of the same biomarker (expressed, for example, in ng/ml) in a corresponding control/normal sample or group of control/normal samples obtained from normal, or healthy, subjects, i.e., subject who do not have brain injury. Further, the term "altered level of expression" of a biomarker in a sample refers to a level that is either below or above the predetermined threshold value of expression for the same biomarker and thus encompasses either high (increased) or low (decreased) expression levels.

The terms "specifically binds to," "specific for," and related grammatical variants refer to that binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M. As used herein, the terms "specific binding" or "specifically binding" when used in reference to the interaction of an antibody and a protein or peptide means that the interaction is dependent upon the presence of a particular structure (i.e., the epitope) on the protein.

As used herein, the terms "binding agent specific for" or "binding agent that specifically binds" refers to an agent that binds to a biomarker and does not significantly bind to unrelated compounds. Examples of binding agents that can be effectively employed in the disclosed methods include, but are not limited to, proteins and antibodies, such as monoclonal or polyclonal antibodies, or antigen-binding fragments thereof. In certain embodiments, a binding agent binds a biomarker (e.g., a polypeptide biomarker) with an affinity constant of, for example, greater than or equal to about $1\times10^{-6}$ M.

II. Detection of Brain Injury Biomarkers

A. Detection by Immunoassay

In other embodiments, the biomarkers of the present invention can be detected and/or measured by immunoassay Immunoassay requires biospecific capture reagents/binding agent, such as antibodies, to capture the biomarkers. Many antibodies are available commercially. Antibodies also can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well-known in the art.

The present invention contemplates traditional immunoassays including, for example, sandwich immunoassays including ELISA or fluorescence-based immunoassays, immunoblots, Western Blots (WB), as well as other enzyme immunoassays. Nephelometry is an assay performed in liquid phase, in which antibodies are in solution. Binding of the antigen to the antibody results in changes in absorbance, which is measured. In a SELDI-based immunoassay, a biospecific capture reagent for the biomarker is attached to the surface of an MS probe, such as a pre-activated protein chip array. The biomarker is then specifically captured on the biochip through this reagent, and the captured biomarker is detected by mass spectrometry.

In certain embodiments, the expression levels of the biomarkers employed herein are quantified by immunoassay, such as enzyme-linked immunoassay (ELISA) technology. In specific embodiments, the levels of expression of the biomarkers are determined by contacting the biological sample with antibodies, or antigen binding fragments thereof, that selectively bind to the biomarkers; and detecting binding of the antibodies, or antigen binding fragments thereof, to the biomarkers. In certain embodiments, the binding agents employed in the disclosed methods and compositions are labeled with a detectable moiety.

For example, the level of a biomarker in a sample can be assayed by contacting the biological sample with an antibody, or antigen binding fragment thereof, that selectively binds to the target biomarker (referred to as a capture molecule or antibody or a binding agent), and detecting the binding of the antibody, or antigen-binding fragment thereof, to the biomarker. The detection can be performed using a second antibody to bind to the capture antibody complexed with its target biomarker. A target biomarker can be an entire protein, or a variant or modified form thereof. Kits for the detection of biomarkers as described herein can include pre-coated strip plates, biotinylated secondary antibody, standards, controls, buffers, streptavidin-horse radish peroxidise (HRP), tetramethyl benzidine (TMB), stop reagents, and detailed instructions for carrying out the tests including performing standards.

The present disclosure also provides methods for identifying which patients with brain injury require a head CT, diagnosing brain injury in a subject, etc. wherein the levels of expression of the biomarkers in a biological sample are determined simultaneously. For example, in one embodiment, methods are provided that comprise: (a) contacting a biological sample obtained from the subject with a plurality of binding agents that selectively bind to a plurality of biomarkers disclosed herein for a period of time sufficient to form binding agent-biomarker complexes; (b) detecting binding of the binding agents to the plurality of biomarkers, thereby determining the levels of expression of the biomarkers in the biological sample; and (c) comparing the levels of expression of the plurality of biomarkers in the biological sample with predetermined threshold values, wherein levels of expression of at least one of the plurality of polypeptide biomarkers above the predetermined threshold values indicates, for example, a brain injury in the subject, indicates the necessity of a heat CT, indicates a patient as likely having ICH, or indicates a likelihood of short and long-term post-concussive symptoms and disability after TBI. Examples of binding agents that can be effectively employed in such methods include, but are not limited to, antibodies or antigen-binding fragments thereof, aptamers, lectins and the like.

In a further aspect, the present disclosure provides compositions that can be employed in the disclosed methods. In certain embodiments, such compositions a solid substrate and a plurality of binding agents immobilized on the substrate, wherein each of the binding agents is immobilized at a different, indexable, location on the substrate and the binding agents selectively bind to a plurality of biomarkers disclosed herein. In a specific embodiment, the locations are pre-determined. In one embodiment, the binding agents selectively bind to a plurality of biomarkers comprising GFAP, S100B, MT3, ICAM5, BDNF, and/or NSE. In other embodiments, such compositions additionally comprise binding agents that selectively bind to other brain injury biomarkers. Binding agents that can be employed in such compositions include, but are not limited to, antibodies, or antigen-binding fragments thereof, aptamers, lectins and the like.

In a related aspect, methods for diagnosing the presence of brain injury in a subject are provided, such methods comprising: (a) contacting a biological sample obtained from the subject with a composition disclosed herein for a period of time sufficient to form binding agent-polypeptide biomarker complexes; (b) detecting binding of the plurality of binding agents to the plurality of polypeptide biomarkers, thereby determining the levels of expression of the plurality of polypeptide biomarkers in the biological sample; and (c) comparing the levels of expression of the plurality of polypeptide biomarkers in the biological sample with predetermined threshold values, wherein levels of expression of at least two of the plurality of polypeptide biomarkers above the predetermined threshold values indicates the presence of brain injury in the subject.

In yet another aspect, the present disclosure provides compositions comprising a solid substrate and a plurality of polypeptide biomarkers disclosed herein immobilized on the substrate, wherein each of the polypeptide biomarkers is immobilized at a different, indexable, location on the substrate. In certain embodiments, the plurality of polypeptide biomarkers includes GFAP, S100B, MT3, ICAM5, BDNF, and/or NSE. In other embodiments, the plurality of polypeptide biomarkers further includes at least one polypeptide biomarker selected from the group consisting of NRGN, MBP, PAD-2, tubulin beta-4B chain, tubulin alpha-1B chain, CNPase, PPIA, Septin-7, Elongation factor1-alpha2, TPPP, TPPP3, Ermin Isoform 2, NDRG2 Isoform 2, ASTN1, BAI3; CNDP1; ERMIN; GRM3; KLH32; MAGE2; NRG3; OMG; solute carrier family 39 (zinc transporter); RTN1; and PAD.

Although antibodies are useful because of their extensive characterization, any other suitable agent (e.g., a peptide, an aptamer, or a small organic molecule) that specifically binds a biomarker of the present invention is optionally used in place of the antibody in the above described immunoassays. For example, an aptamer that specifically binds a biomarker and/or one or more of its breakdown products might be used. Aptamers are nucleic acid-based molecules that bind specific ligands. Methods for making aptamers with a particular binding specificity are known as detailed in U.S. Pat. Nos. 5,475,096; 5,670,637; 5,696,249; 5,270,163; 5,707,796; 5,595,877; 5,660,985; 5,567,588; 5,683,867; 5,637,459; and 6,011,020.

In specific embodiments, the assay performed on the biological sample can comprise contacting the biological sample with one or more capture agents (e.g., antibodies, peptides, aptamer, etc., combinations thereof) to form a biomarker:capture agent complex. The complexes can then be detected and/or quantified. A subject can then be identified as having brain injury based on a comparison of the detected/quantified/measured levels of biomarkers to one or more reference controls as described herein.

In one method, a first, or capture, binding agent, such as an antibody that specifically binds the biomarker of interest, is immobilized on a suitable solid phase substrate or carrier. The test biological sample is then contacted with the capture antibody and incubated for a desired period of time. After washing to remove unbound material, a second, detection, antibody that binds to a different, non-overlapping, epitope on the biomarker is then used to detect binding of the polypeptide biomarker to the capture antibody. The detection antibody is preferably conjugated, either directly or indirectly, to a detectable moiety. Examples of detectable moieties that can be employed in such methods include, but are not limited to, cheminescent and luminescent agents; fluorophores such as fluorescein, rhodamine and eosin; radioisotopes; colorimetric agents; and enzyme-substrate labels, such as biotin.

In another embodiment, the assay is a competitive binding assay, wherein labeled biomarker is used in place of the labeled detection antibody, and the labeled biomarker and any unlabeled biomarker present in the test sample compete for binding to the capture antibody. The amount of biomarker bound to the capture antibody can be determined based on the proportion of labeled biomarker detected.

Solid phase substrates, or carriers, that can be effectively employed in such assays are well known to those of skill in the art and include, for example, 96 well microtiter plates, glass, paper, and microporous membranes constructed, for example, of nitrocellulose, nylon, polyvinylidene difluoride, polyester, cellulose acetate, mixed cellulose esters and polycarbonate. Suitable microporous membranes include, for example, those described in US Patent Application Publication no. US 2010/0093557 A1. Methods for the automation of immunoassays are well known in the art and include, for example, those described in U.S. Pat. Nos. 5,885,530, 4,981,785, 6,159,750 and 5,358,691.

The presence of several different polypeptide biomarkers in a test sample can be detected simultaneously using a multiplex assay, such as a multiplex ELISA. Multiplex assays offer the advantages of high throughput, a small volume of sample being required, and the ability to detect different proteins across a board dynamic range of concentrations.

In certain embodiments, such methods employ an array, wherein multiple binding agents (for example capture antibodies) specific for multiple biomarkers are immobilized on a substrate, such as a membrane, with each capture agent being positioned at a specific, pre-determined, location on the substrate. Methods for performing assays employing such arrays include those described, for example, in US Patent Application Publication nos. US2010/0093557A1 and US2010/0190656A1, the disclosures of which are hereby specifically incorporated by reference.

Multiplex arrays in several different formats based on the utilization of, for example, flow cytometry, chemiluminescence or electron-chemiluminesence technology, are well known in the art. Flow cytometric multiplex arrays, also known as bead-based multiplex arrays, include the Cytometric Bead Array (CBA) system from BD Biosciences (Bedford, Mass.) and multi-analyte profiling (xMAP®) technology from Luminex Corp. (Austin, Tex.), both of which employ bead sets which are distinguishable by flow cytometry. Each bead set is coated with a specific capture antibody. Fluorescence or streptavidin-labeled detection antibodies bind to specific capture antibody-biomarker complexes formed on the bead set. Multiple biomarkers can be recognized and measured by differences in the bead sets, with chromogenic or fluorogenic emissions being detected using flow cytometric analysis.

In an alternative format, a multiplex ELISA from Quansys Biosciences (Logan, Utah) coats multiple specific capture antibodies at multiple spots (one antibody at one spot) in the same well on a 96-well microtiter plate. Chemiluminescence technology is then used to detect multiple biomarkers at the corresponding spots on the plate.

B. Detection by Polymerase Chain Reaction

In certain embodiments, the biomarkers of the present invention can be detected/measure/quantitated by polymerase chain reaction (PCR). In certain embodiments, the present invention contemplates quantitation of one or more biomarkers described herein including GFAP, S100B, MT3, ICAM5, BDNF, and/or NSE. The one or more biomarkers can be quantitated and the expression can be compared to reference levels. Overexpression or underexpression, depending on the biomarker, relative to the reference is indicative of injury. PCR can include quantitative type PCR, such as quantitative, real-time PCR (both singleplex and multiplex). In a specific embodiment, the quantitation steps are carried using quantitative, real-time PCR. One of ordinary skill in the art can design primers that specifically bind and amplify one or more biomarkers described herein using the publicly available sequences thereof.

In more particular embodiments, an assay performed on a biological sample obtained from a subject may comprise extracting nucleic acids from the biological sample. The assay can further comprise contacting nucleic acids with one or more primers that specifically bind one or more biomarker described herein to form a primer:biomarker complex. The assay can further comprise the step of amplifying the primer:biomarker complexes. The amplified complexes can then be detected/quantified to determine a level of expression of the one or more biomarkers. A subject can then be identified as having a brain injury based on a comparison of the measure/quantified/determined levels of one or more biomarkers described herein to one or more reference controls as described herein. The subject can then be treated appropriately, based on the grade/extent of injury. The assay can be performed on mRNA extracted from the biological sample.

C. Detection by Mass Spectrometry

In one aspect, the biomarkers of the present invention may be detected by mass spectrometry, a method that employs a mass spectrometer to detect gas phase ions. Examples of mass spectrometers are time-of-flight, magnetic sector, quadrupole filter, ion trap, ion cyclotron resonance, Orbitrap, hybrids or combinations of the foregoing, and the like.

In particular embodiments, the biomarkers of the present invention are detected using selected reaction monitoring (SRM) mass spectrometry techniques. Selected reaction monitoring (SRM) is a non-scanning mass spectrometry technique, performed on triple quadrupole-like instruments and in which collision-induced dissociation is used as a means to increase selectivity. In SRM experiments two mass analyzers are used as static mass filters, to monitor a particular fragment ion of a selected precursor ion. The specific pair of mass-over-charge (m/z) values associated to the precursor and fragment ions selected is referred to as a "transition" and can be written as parent m/z→fragment m/z (e.g. 673.5→534.3). Unlike common MS based proteomics, no mass spectra are recorded in a SRM analysis. Instead, the detector acts as counting device for the ions matching the selected transition thereby returning an intensity distribution over time. Multiple SRM transitions can be measured within the same experiment on the chromatographic time scale by rapidly toggling between the different precursor/fragment pairs (sometimes called multiple reaction monitoring, MRM). Typically, the triple quadrupole instrument cycles through a series of transitions and records the signal of each transition as a function of the elution time. The method allows for additional selectivity by monitoring the chromatographic coelution of multiple transitions for a given analyte. The terms SRM/MRM are occasionally used also to describe experiments conducted in mass spectrometers other than triple quadrupoles (e.g. in trapping instruments) where upon fragmentation of a specific precursor ion a narrow mass range is scanned in MS2 mode, centered on a fragment ion specific to the precursor of interest or in general in experiments where fragmentation in the collision cell is used as a means to increase selectivity. In this application the terms SRM and MRM or also SRM/MRM can be used interchangeably, since they both refer to the same mass spectrometer operating principle. As a matter of clarity, the term MRM is used throughout the text, but the term includes both SRM and MRM, as well as any analogous technique, such as e.g. highly-selective reaction monitoring, hSRM, LC-SRM or any other SRM/MRM-like or SRM/MRM-mimicking approaches performed on any type of mass spectrometer and/or, in which the peptides are fragmented using any other fragmentation method such as e.g. CAD (collision-activated dissociation (also known as CID or collision-induced dissociation), HCD (higher energy CID), ECD (electron capture dissociation), PD (photodissociation) or ETD (electron transfer dissociation).

In another specific embodiment, the mass spectrometric method comprises matrix assisted laser desorption/ionization time-of-flight (MALDI-TOF MS or MALDI-TOF). In another embodiment, method comprises MALDI-TOF tandem mass spectrometry (MALDI-TOF MS/MS). In yet another embodiment, mass spectrometry can be combined with another appropriate method(s) as may be contemplated by one of ordinary skill in the art. For example, MALDI-TOF can be utilized with trypsin digestion and tandem mass spectrometry as described herein.

In an alternative embodiment, the mass spectrometric technique comprises surface enhanced laser desorption and ionization or "SELDI," as described, for example, in U.S. Pat. Nos. 6,225,047 and 5,719,060. Briefly, SELDI refers to a method of desorption/ionization gas phase ion spectrometry (e.g. mass spectrometry) in which an analyte (here, one or more of the biomarkers) is captured on the surface of a SELDI mass spectrometry probe. There are several versions of SELDI that may be utilized including, but not limited to, Affinity Capture Mass Spectrometry (also called Surface-Enhanced Affinity Capture (SEAC)), and Surface-Enhanced Neat Desorption (SEND) which involves the use of probes comprising energy absorbing molecules that are chemically bound to the probe surface (SEND probe). Another SELDI method is called Surface-Enhanced Photolabile Attachment and Release (SEPAR), which involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker panel, pursuant to the present invention.

In another mass spectrometry method, the biomarkers can be first captured on a chromatographic resin having chromatographic properties that bind the biomarkers. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

D. Detection by Electrochemicaluminescent Assay

In several embodiments, the biomarker biomarkers of the present invention may be detected by means of an electrochemicaluminescent assay developed by Meso Scale Discovery (Gaithersrburg, Md.). Electrochemiluminescence detection uses labels that emit light when electrochemically stimulated. Background signals are minimal because the stimulation mechanism (electricity) is decoupled from the signal (light). Labels are stable, non-radioactive and offer a choice of convenient coupling chemistries. They emit light at ~620 nm, eliminating problems with color quenching. See U.S. Pat. Nos. 7,497,997; 7,491,540; 7,288,410; 7,036,946; 7,052,861; 6,977,722; 6,919,173; 6,673,533; 6,413,783; 6,362,011; 6,319,670; 6,207,369; 6,140,045; 6,090,545; and 5,866,434. See also U.S. Patent Applications Publication No. 2009/0170121; No. 2009/006339; No. 2009/0065357; No. 2006/0172340; No. 2006/0019319; No. 2005/0142033; No. 2005/0052646; No. 2004/0022677; No. 2003/0124572; No. 2003/0113713; No. 2003/0003460; No. 2002/0137234; No. 2002/0086335; and No. 2001/0021534.

E. Other Methods for Detecting Biomarkers

The biomarkers of the present invention can be detected by other suitable methods. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Furthermore, a sample may also be analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there. Protein biochips are biochips adapted for the capture of polypeptides. Many protein biochips are described in the art. These include, for example, protein biochips produced by Ciphergen Biosystems, Inc. (Fremont, Calif.), Invitrogen Corp. (Carlsbad, Calif.), Affymetrix, Inc. (Fremong, Calif.), Zyomyx (Hayward, Calif.), R&D Systems, Inc. (Minneapolis, Minn.), Biacore (Uppsala, Sweden) and Procognia (Berkshire, UK). Examples of such protein biochips are described in the following patents or published patent applications: U.S. Pat. Nos. 6,537,749; 6,329,209; 6,225,047; 5,242,828; PCT International Publication No. WO 00/56934; and PCT International Publication No. WO 03/048768.

III. Determination of a Patient's Brain Injury Status

A. The present invention relates to the use of biomarkers to diagnose brain injury, to determine whether a patient requires a head CT, to identify a patient with TBI as likely having ICH, and/or to predict short and long-term post-concussive symptoms and disability after TBI. It is understood that, for the sake of brevity, the term "brain injury" is used throughout the specification, but it is understood that the methods and biomarkers described herein are applicable in the context of diagnosing neurodegeneration. More specifically, the biomarkers of the present invention can be used in diagnostic tests to determine, qualify, and/or assess brain injury or status, for example, to diagnose brain injury, in an individual, subject or patient. In particular embodiments, brain injury status can include determining a patient's brain injury status or brain injury status, for example, to diagnose brain injury, in an individual, subject or patient. More specifically, the biomarkers to be detected in diagnosing brain injury (e.g., subclinical or traumatic brain injury) include, but are not limited to, GFAP, S100B, MT3, ICAM5, BDNF, and/or NSE. Other biomarkers known in the relevant art may be used in combination with the biomarkers described herein. The present invention further contemplates the detection, measurement, quantification, determination and the like of both unmodified and modified (e.g., citrullination or other post-translational modification) proteins/polypeptides/peptides as well as autoantibodies to any of the foregoing, determining a patient's brain injury status. It is understood that the methods and compositions described herein can not only be used to diagnose brain injury, but also other brain in injury statuses/conditions including to determine whether a patient requires a head CT, to identify a patient with TBI as likely having ICH, and/or to predict short and long-term post-concussive symptoms and disability after TBI.

B. Biomarker Panels

The biomarkers of the present invention can be used in diagnostic tests to assess, determine, and/or qualify (used interchangeably herein) brain injury status in a patient. The phrase "brain injury status" includes any distinguishable manifestation of the condition, including not having brain injury. For example, brain injury status includes, without limitation, the presence or absence of brain injury in a patient, the risk of developing brain injury, the stage or severity of brain injury, the progress of brain injury (e.g., progress of brain injury over time), the effectiveness or response to treatment of brain injury (e.g., clinical follow up and surveillance of brain injury after treatment), whether a patient requires a head CT, whether a patient with TBI as likely having ICH, and/or to predict short and long-term post-concussive symptoms and disability after TBI. Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker panels of the present invention may show a statistical difference in different brain injury statuses of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9.

The biomarkers can be differentially present in UI (NC or non-brain injury) and brain injury, and, therefore, are useful in aiding in the determination of brain injury status. In certain embodiments, the biomarkers are measured in a patient sample using the methods described herein and compared, for example, to predefined biomarker levels/ratios and correlated to brain injury status. In particular embodiments, the measurement(s) may then be compared with a relevant diagnostic amount(s), cut-off(s), or multivariate model scores that distinguish a positive brain injury status from a negative brain injury status. The diagnostic amount(s) represents a measured amount of a biomarker(s) above which or below which a patient is classified as having a particular brain injury status. For example, if the biomarker(s) is/are up-regulated compared to normal during brain injury, then a measured amount(s) above the diagnostic cutoff(s) provides a diagnosis of brain injury. Alternatively, if the biomarker(s) is/are down-regulated during brain injury, then a measured amount(s) at or below the diagnostic cutoff(s) provides a diagnosis of non-brain injury. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarkers in a statistically significant number of samples from patients with the different brain injury statuses, and drawing the cut-off to suit the desired levels of specificity and sensitivity.

In other embodiments, ratios of post-translationally modified biomarkers to the corresponding unmodified biomarkers are useful in aiding in the determination of brain injury status. In certain embodiments, the biomarker ratios are indicative of diagnosis. In other embodiments, a biomarker ratio can be compared to another biomarker ratio in the same sample or to a set of biomarker ratios from a control or reference sample.

Indeed, as the skilled artisan will appreciate there are many ways to use the measurements of two or more biomarkers in order to improve the diagnostic question under investigation. In a quite simple, but nonetheless often effective approach, a positive result is assumed if a sample is positive for at least one of the markers investigated.

Furthermore, in certain embodiments, the values measured for markers of a biomarker panel are mathematically combined and the combined value is correlated to the underlying diagnostic question. Biomarker values may be combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating a biomarker combination of the present invention, e.g. to diagnose brain injury, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

C. Determining Risk of Developing Brain Injury

In a specific embodiment, the present invention provides methods for determining the risk of developing brain injury in a patient. Biomarker percentages, ratios, amounts or patterns are characteristic of various risk states, e.g., high, medium or low. The risk of developing brain injury is determined by measuring the relevant biomarkers and then either submitting them to a classification algorithm or comparing them with a reference amount, i.e., a predefined level or pattern of biomarkers that is associated with the particular risk level.

D. Determining Brain Injury Severity

In another embodiment, the present invention provides methods for determining the severity of brain injury in a patient. Each grade or stage of brain injury likely has a characteristic level of a biomarker or relative levels/ratios of a set of biomarkers (a pattern or ratio). The severity of brain injury is determined by measuring the relevant biomarkers and then either submitting them to a classification algorithm or comparing them with a reference amount, i.e., a predefined level or pattern of biomarkers that is associated with the particular stage.

E. Determining Brain Injury Prognosis

In one embodiment, the present invention provides methods for determining the course of brain injury in a patient. Brain injury course refers to changes in brain injury status over time, including brain injury progression (worsening) and brain injury regression (improvement). Over time, the amount or relative amount (e.g., the pattern or ratio) of the biomarkers changes. For example, biomarker "X" may be increased with brain injury, while biomarker "Y" may be decreased with brain injury. Therefore, the trend of these biomarkers, either increased or decreased over time toward brain injury or non-brain injury indicates the course of the condition. Accordingly, this method involves measuring the level of one or more biomarkers in a patient at least two different time points, e.g., a first time and a second time, and comparing the change, if any. The course of brain injury is determined based on these comparisons.

F. Patient Management

In certain embodiments of the methods of qualifying brain injury status, the methods further comprise managing patient treatment based on the status. Such management includes the actions of the physician or clinician subsequent to determining brain injury status. For example, if a physician makes a diagnosis of brain injury, then a certain regime of monitoring would follow. An assessment of the course of brain injury using the methods of the present invention may then require a certain brain injury therapy regimen. Alternatively, a diagnosis of non-brain injury might be followed with further testing to determine a specific disease that the patient might be suffering from. Also, further tests may be called for if the diagnostic test gives an inconclusive result on brain injury status.

G. Determining Therapeutic Efficacy of Pharmaceutical Drug

In another embodiment, the present invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern, profile or ratio) of one or more of the biomarkers of the present invention may change toward a non-brain injury profile. Therefore, one can follow the course of one or more biomarkers in the patient during the course of treatment. Accordingly, this method involves measuring one or more biomarkers in a patient receiving drug therapy, and correlating the biomarker levels/ratios with the brain injury status of the patient (e.g., by comparison to predefined levels/ratios of the biomarkers that correspond to different brain injury statuses). One embodiment of this method involves determining the levels/ratios of one or more biomarkers for at least two different time points during a course of drug therapy, e.g., a first time and a second time, and comparing the change in levels/ratios of the biomarkers, if any. For example, the levels/ratios of one or more biomarkers can be measured before and after drug administration or at two different time points during drug administration. The effect of therapy is determined based on these comparisons. If a treatment is effective, then the level/ratio of one or more biomarkers will trend toward normal, while if treatment is ineffective, the level/ratio of one or more biomarkers will trend toward brain injury indications.

H. Generation of Classification Algorithms for Qualifying Brain Injury Status

In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition (e.g., diseased versus non-diseased).

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarkers already discovered, and for finding new biomarker biomarkers. The classification algorithms, in turn, form the base for diagnostic tests by providing diagnostic values (e.g., cut-off points) for biomarkers used singly or in combination.

IV. Kits for the Detection of Brain Injury Biomarkers

In another aspect, the present invention provides kits for qualifying brain injury status, which kits are used to detect the biomarkers described herein. In a specific embodiment, the kit is provided as an ELISA kit comprising antibodies to the biomarkers of the present invention including, but not limited to, GFAP, S100B, MT3, ICAM5, BDNF, and/or NSE.

The ELISA kit may comprise a solid support, such as a chip, microtiter plate (e.g., a 96-well plate), bead, or resin having biomarker capture reagents attached thereon. The kit may further comprise a means for detecting the biomarkers, such as antibodies, and a secondary antibody-signal complex such as horseradish peroxidase (HRP)-conjugated goat anti-rabbit IgG antibody and tetramethyl benzidine (TMB) as a substrate for HRP.

The kit for qualifying brain injury status may be provided as an immuno-chromatography strip comprising a membrane on which the antibodies are immobilized, and a means for detecting, e.g., gold particle bound antibodies, where the membrane, includes NC membrane and PVDF membrane. The kit may comprise a plastic plate on which a sample application pad, gold particle bound antibodies temporally immobilized on a glass fiber filter, a nitrocellulose membrane on which antibody bands and a secondary antibody band are immobilized and an absorbent pad are positioned in a serial manner, so as to keep continuous capillary flow of blood serum.

In certain embodiments, a patient can be diagnosed by adding blood or blood serum from the patient to the kit and detecting the relevant biomarkers conjugated with antibodies, specifically, by a method which comprises the steps of: (i) collecting blood or blood serum from the patient; (ii) separating blood serum from the patient's blood; (iii) adding the blood serum from patient to a diagnostic kit; and, (iv) detecting the biomarkers conjugated with antibodies. In this method, the antibodies are brought into contact with the patient's blood. If the biomarkers are present in the sample, the antibodies will bind to the sample, or a portion thereof. In other kit and diagnostic embodiments, blood or blood serum need not be collected from the patient (i.e., it is already collected). Moreover, in other embodiments, the sample may comprise a tissue sample or a clinical sample.

The kit can also comprise a washing solution or instructions for making a washing solution, in which the combination of the capture reagents and the washing solution allows capture of the biomarkers on the solid support for subsequent detection by, e.g., antibodies or mass spectrometry. In a further embodiment, a kit can comprise instructions for suitable operational parameters in the form of a label or separate insert. For example, the instructions may inform a consumer about how to collect the sample, how to wash the probe or the particular biomarkers to be detected, etc. In yet another embodiment, the kit can comprise one or more containers with biomarker samples, to be used as standard(s) for calibration.

In another specific embodiment, the kit is provided as a PCR kit comprising primers that specifically bind to one or more of the nucleic acid biomarkers described herein. One of ordinary skill in the art can design primers the specifically bind and amplify the target biomarkers described herein including GFAP, S100B, MT3, ICAM5, BDNF, and/or NSE. The kit can further comprise substrates and other reagents necessary for conducting PCR (e.g., quantitative real-time PCR). The kit can be configured to conduct singleplex or multiplex PCR. The kit can further comprise instructions for carrying out the PCR reaction(s). In specific embodiments, the biological sample obtained from a subject may be manipulated to extract nucleic acid. In a further embodiment, the nucleic acids are contacted with primers that specifically bind the target biomarkers to form a primer:biomarker complex. The complexes can then be amplified and detected/quantified/measured to determine the levels of one or more biomarkers. The subject can then be identified as having brain injury based on a comparison of the measured levels of one or more biomarkers to one or more reference controls.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Using a multi-biomarker approach, we have identified that specific combinations of brain injury biomarkers and/or their variants outperform single biomarkers in predicting intracranial hemorrhage. In addition, BDNF predicts persistent post-concussive symptoms with excellent diagnostic accuracy. Similarly, GFAP predicts short-term disability with an accuracy equal or superior to head CT, the gold standard test. As circulating BDNF levels decrease with concussion, BDNF could serve as biomarker of concussion, or return to play or work. As BDNF is an essential neurotrophic factor, BDNF or BDNF receptor analogues could have therapeutic potential in TBI and other brain injury or disease (where there is cell death or trauma).

Example 1: Use of Protein Biomarker Panels for Acute Traumatic Brain Injury (TBI) at Time of Presentation Combinations of protein biomarkers and their variants (including protein splice variants (isoforms), polymorphisms, and degraded and other post-translational modifications including, but not limited to, citrullination, phosphorylation, acetylation, methylation, etc.) used as a screening test prior to obtaining a head computerized tomography (CT) scan for diagnosing acute intracranial pathology will allow a safe decrease in avoidable head CT scans.

Materials and Methods

Study Design:
Case control.
Study Population. TBI Cases:
Cases were consecutive adult patients (18 years or older) presenting to the Johns Hopkins Hospital Emergency Department (ED) with blunt trauma to the head that occurred within 24 hours of arrival, who had a head CT scan that demonstrated acute traumatic intracranial hemorrhage, and who additionally, had excess serum specimen available in the clinical chemistry laboratory. Patients were excluded if they had prior brain surgery or a brain tumor.

TBI Controls:

TBI Controls were consecutive adult patients (18 years or older) who presented to the Johns Hopkins Hospital ED within 5 days of cases, for blunt head trauma significant enough to warrant receiving a head CT scan as part of their ED evaluation, but did not have intracranial hemorrhage (i.e., only concussion). Furthermore, patients were included as controls if they had excess serum specimen available in the clinical chemistry laboratory.

Non-TBI Controls:

Adult patients (18 years or older) who presented to the Johns Hopkins Hospital Emergency Department, who were evaluated for acute coronary syndrome and were ultimately discharged home with a non-cardiac diagnosis. These patients did not have acute trauma or focal neurological deficits. No CT scan was carried out on this population. Furthermore, control patients provided written informed consent for blood samples to be drawn for research purposes.

Timing of Blood Draw.

Serum samples were obtained at Emergency Department presentation.

Biomarker Assays.

High sensitivity ELISA assays, developed in Dr. Everett's laboratory for GFAP (glial fibrillary acidic protein), ICAM5 (intracellular adhesion molecule 5), S100B, MT3 (metallothionein 3), neuron specific enolase (NSE) and BDNF (brain derived neurotrophic factor), were used. Protein standards for GFAP, ICAM5, S100B, NSE and BDNF were from commercial sources and for MT3, developed in Dr. Everett's laboratory at Johns Hopkins University.

Results

Figure 2:
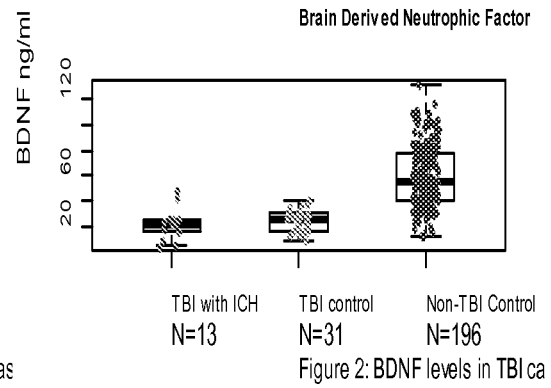
FIG. 2. BDNF levels in TBI cases and controls.
Figure 3:
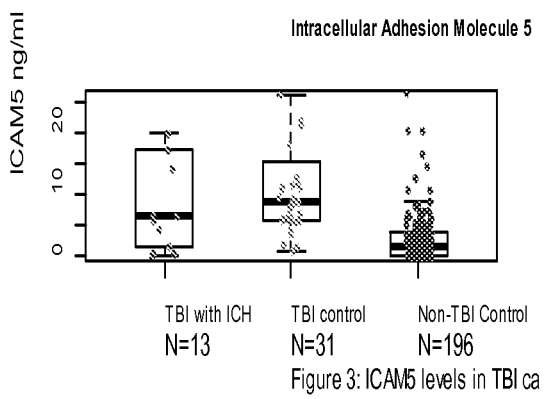
FIG. 3. ICAM5 levels in TBI cases and controls.
Figure 4:
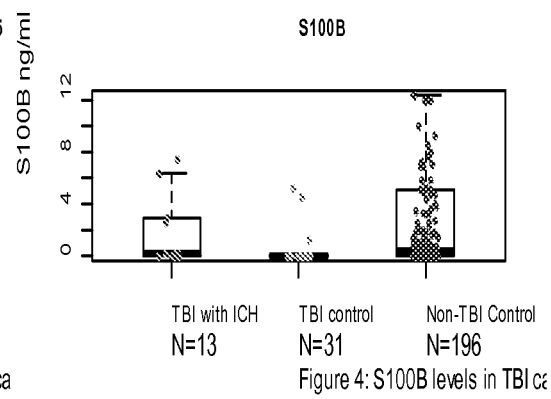
FIG. 4. S100B levels in TBI cases and controls.
Figure 5:
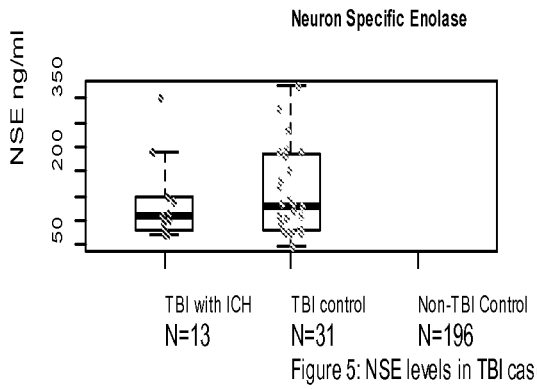
FIG. 5. NSE levels in TBI cases and controls.
Figure 6:
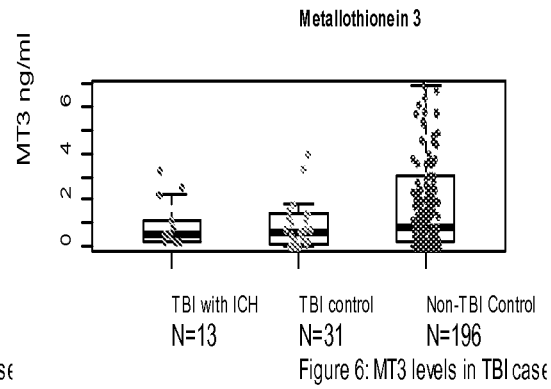
FIG. 6. MT3 levels in TBI cases and controls.
Figure 7:
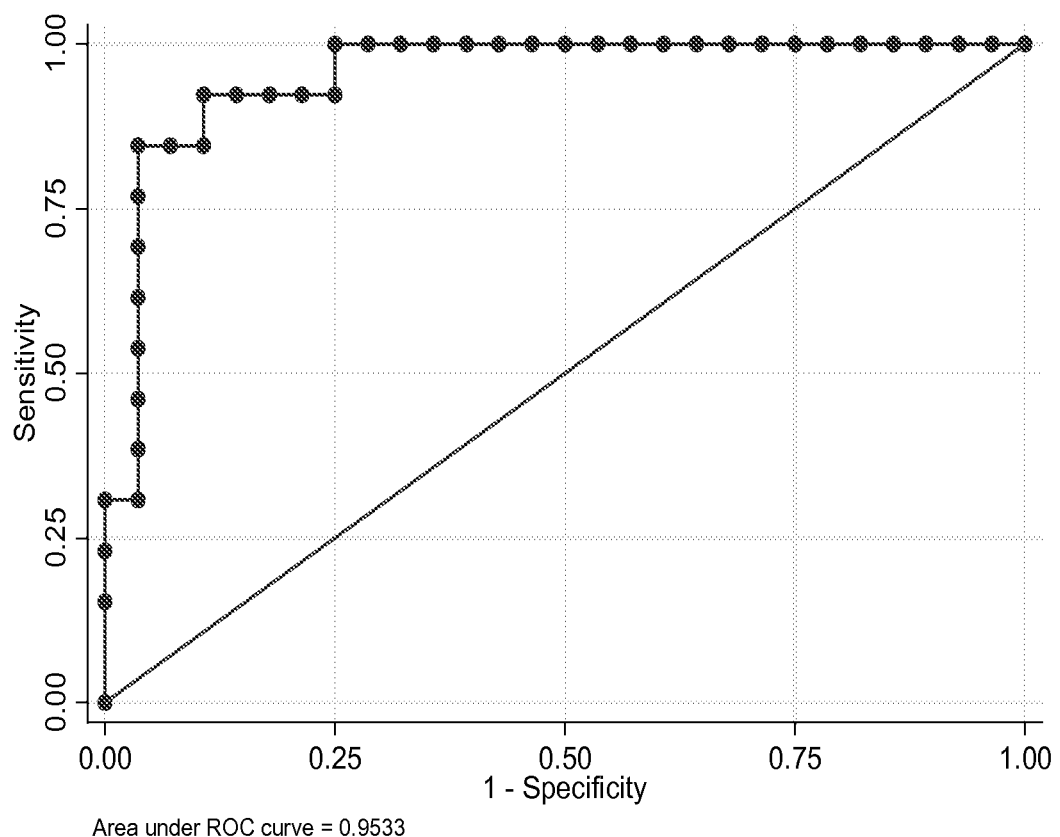
FIG. 7. Receiver operator curve for logistic regression model including GFAP, S100B and NSE. The area under the ROC curve for this combination of proteins is 0.95.
Figure 8:
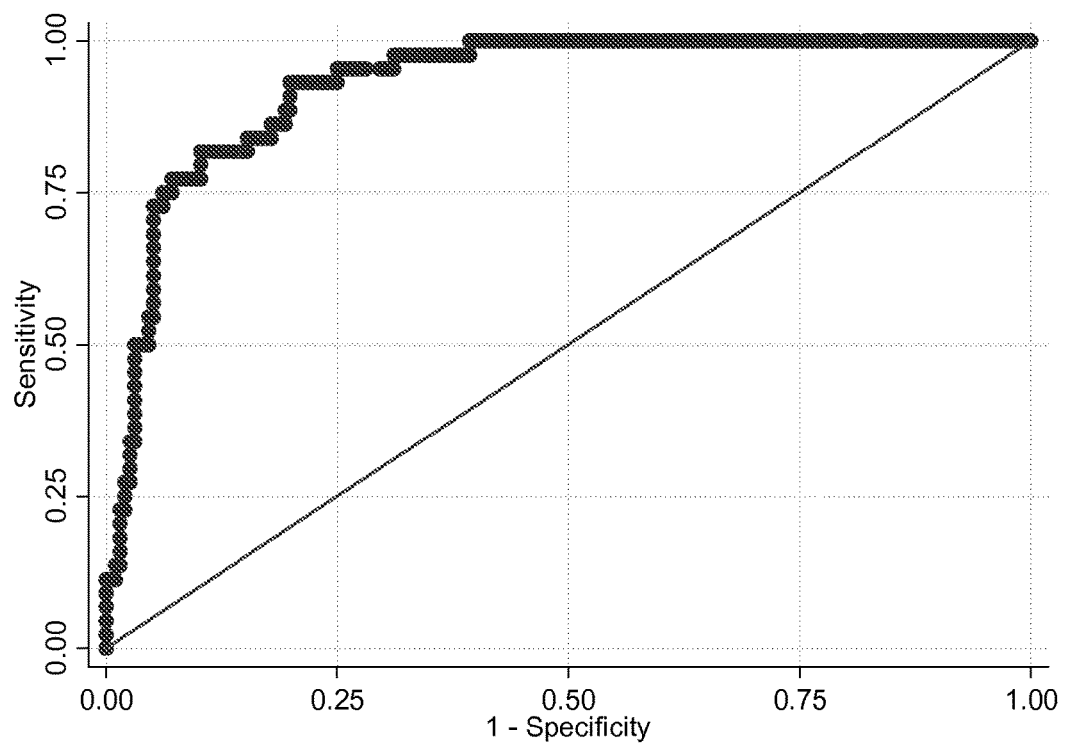
FIG. 8. Receiver operator curve for BDNF. The area under ROC curve for BDNF is 0.9292.
Figure 9:
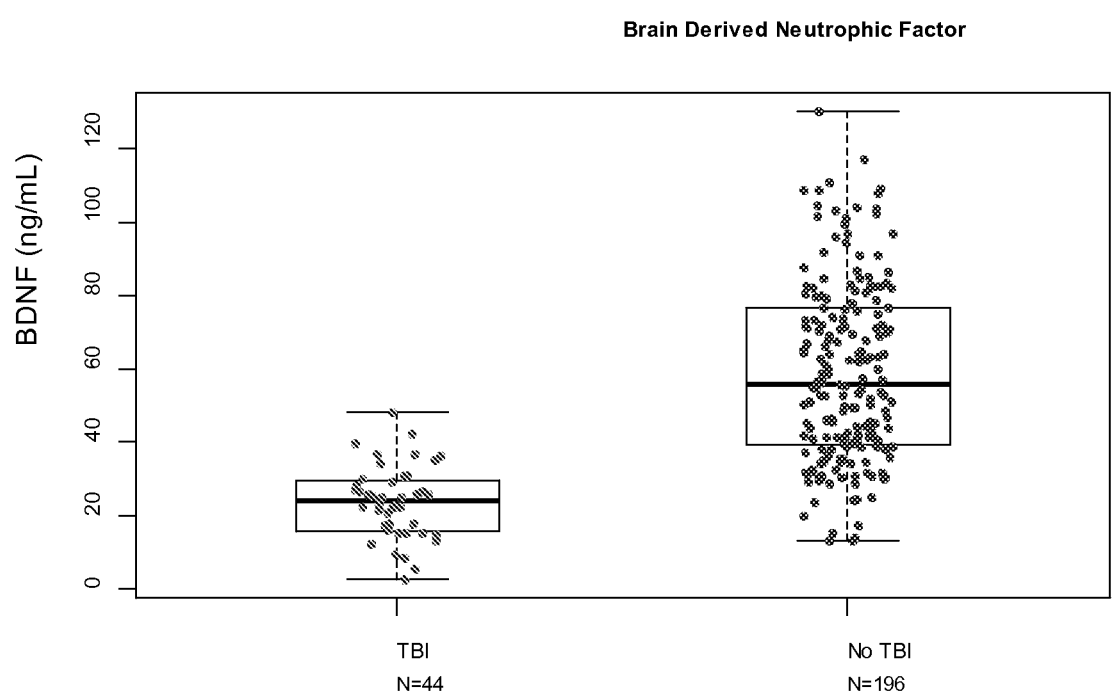
FIG. 9. BDNF levels in TBI cases and controls.
Figure 10:
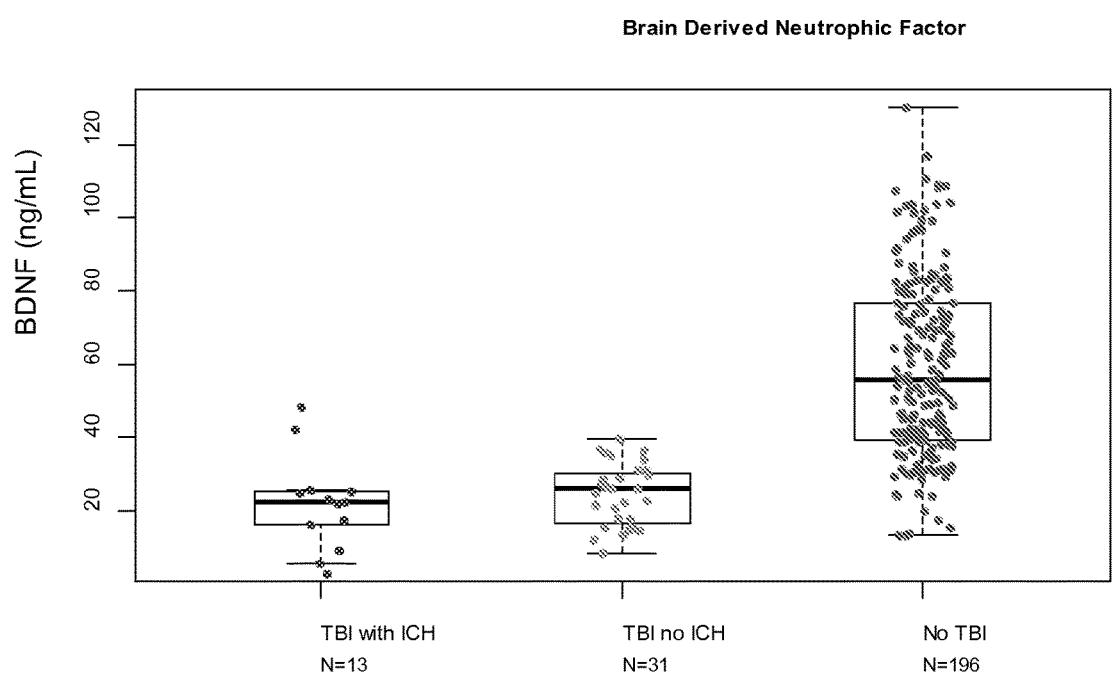
FIG. 10. BDNF levels TBI/ICH cases and controls.

The initial blood draw at the time of admission was analyzed for a total of 13 TBI cases, 31 TBI controls and 196 non-TBI controls by ELISA. The results demonstrate that GFAP (FIG. 1) and ICAM5 (FIG. 3) were both significantly elevated in the TBI group (ICH and No ICH) as compared to S100B (FIG. 4), MT3 (FIG. 6), and BDNF (FIG. 2). Alone GFAP had the greatest ability to predict ICH from no-ICH (FIG. 1). We found that the following combinations of biomarkers allowed us to identify all TBI cases with intracranial hemorrhage (ICH) based on the results from the CT scan taken for the TBI ICH and TBI control, i.e., 100% sensitivity for ICH (Table 1):

GFAP and S100B
GFAP and NSE
GFAP, ICAM5, and S100B
GFAP, ICAM5 and MT3
GFAP, MT3, and ICAM5
GFAP, NSE, and S100B
GFAP, ICAM5, MT3, and S100B Additionally, the use of these combinations of biomarkers as a screening test for ICH, prior to obtaining a head CT will result in avoiding 30-50% of head CT scans with no acute intracranial finding (Table 1).

TABLE 1

Diagnostic Accuracy of Different Biomarker Panels for Discriminating Between Intracranial Hemorrhage and No-Intracranial Hemorrhage Among Patients with Mild Traumatic Brain Injury

| Biomarker | True Positive | True Negative (Avoidable head CTs) | False Positive | False Negative (Missed cases) | Sample Size |
|---|---|---|---|---|---|
| GFAP | 11 | 25 | 6 | 2 | 44 |
| ICAM5 | 4 | 23 | 8 | 9 | 44 |
| S100B | 5 | 25 | 3 | 8 | 41 |
| MT3 | 4 | 18 | 12 | 9 | 43 |
| NSE | 2 | 29 | 2 | 11 | 44 |
| BDNF | 11 | 8 | 23 | 2 | 44 |
| GFAP or S100B | 13 | 22 | 8 | 0 | 43 |
| GFAP or ICAM5 | 11 | 19 | 12 | 2 | 44 |
| GFAP or MT3 | 13 | 17 | 14 | 0 | 44 |
| GFAP or NSE | 13 | 24 | 7 | 0 | 44 |
| GFAP or BDNF | 13 | 5 | 26 | 0 | 44 |
| GFAP or ICAM5 or S100B | 13 | 16 | 14 | 0 | 43 |
| GFAP or ICAM5 or MT3 | 13 | 13 | 18 | 0 | 44 |
| GFAP or MT3 or S100B | 13 | 14 | 17 | 0 | 44 |
| GFAP or NSE or S100B | 13 | 22 | 9 | 0 | 44 |
| GFAP or ICAM5 or MT3 or S100B | 13 | 13 | 18 | 0 | 44 |
| Logistic regression model using GFAP, S100B, NSE | 13 | 21 | 7 | 0 | 41 |

Bold = combinations that avoid the most CT scans.

Definitions: Cut off were for: GFAP: GFAP>0.04 ng/ml; ICAM5: ICAM5>17 ng/ml; S100B: S100B>2 ng/ml; MT3: MT3>0.95 ng/ml; BDNF: BDNF<30 ng/ml; NSE: NSE<71 ng/ml.

Logistic regression model (Table 2): No cut-offs used in the model. Exact biomarker level is entered into the model to produce a probability of having intracranial hemorrhage. Probability>=0.215 if considered high probability for intracranial hemorrhage.

TABLE 2

Biomarker Logistic Regression Model for Probability of Intracranial Hemorrhage

| Biomarker (using logistic regression models) | AUC |
|---|---|
| GFAP AND S100B | 0.91 |
| GFAP AND MT3 | 0.90 |
| GFAP AND NSE | 0.87 |
| GFAP AND ICAM AND S100B | 0.91 |
| GFAP AND ICAM 5 AND MT3 | 0.94 |
| GFAP AND MT3 AND S100B | 0.90 |
| GFAP AND NSE AND S100B | 0.95 |
| GFAP AND ICAM5 AND MT3 AND S100B | 0.91 |

Conclusions

Combinations of the following proteins and their variants (including protein splice variants [isoforms], polymorphisms, and degraded and other post-translational modifications including, but not limited to, citrullination, phosphorylation, acetylation, methylation, etc.: GFAP and/or S100B; GFAP and/or NSE; GFAP and/or ICAM5 and/or S100B; GFAP and/or ICAM5 and/or MT3; GFAP and/or MT3 and/or ICAM5; GFAP and/or NSE and/or S100B; GFAP and/or ICAM5 and/or MT3 and/or S100B when used as a screening test, prior to obtaining a head CT to evaluate for intracranial hemorrhage in TBI, will result in a safe reduction in avoidable head CT scans, without missing ANY patients with intracranial hemorrhage.

Example 2: Brain Derived Neurotrophic Factor (BDNF) and its Variants at Time of Presentation Differentiates Between Patient with and without Traumatic Brain Injury (TBI)

Brain Derived Neurotrophic Factor (BDNF) and its variants (including its splice variants (isoforms), polymorphisms, pro-hormone, active form, pro-hormone inactive cleavage fragment and degraded and other post-translational modifications including, but not limited to, citrullination, phosphorylation, acetylation, methylation and etc., as well as BDNF receptors) at time of presentation differentiates between patient with and without traumatic brain injury (TBI). Furthermore, BDNF, its variants or receptors may be used therapeutically in the treatment of TBI.

Materials and Methods

Study Design.
Case control study.
Study Population. TBI Cases:
Adult patients (18 years or older) presenting to the Johns Hopkins Hospital Emergency Department (ED) with blunt trauma to the head that occurred within 24 hours of arrival, who were deemed by the ED physician to have had significant trauma, enough to obtain a head computerized tomography (CT) scan to evaluate for intracranial hemorrhage. Additionally, cases where patients who had blood drawn for clinical purposes and who also had excess serum specimen in the clinical chemistry laboratory were included.

Non-Trauma Controls:
Adult patients (18 years or older) who presented to the Johns Hopkins University ED, who were evaluated for acute coronary syndrome and were ultimately discharged home with a non-cardiac diagnosis. These patients did not have acute trauma or focal neurological deficits. No head CT scan were performed. Furthermore, control patients provided written informed consent for blood samples to be drawn for research purposes.

Timing of Blood Draw.
Serum samples were obtained at ED presentation.
Biomarker Assays.
High sensitivity ELISA assays, developed in Dr. Everett's laboratory for BDNF (brain derived neurotrophic factor), was used. Protein standards for BDNF were from commercial sources.

Results

There were a total of 44 cases (13 with intracranial hemorrhage and 31 without intracranial hemorrhage based on CT scan) and 196 controls. The median BDNF among cases was 24.1 (IQR: 15.6-29.6) ng/ml and the median BDNF among controls was 55.9 (IQR: 39.3-76.8). Per each ng/ml change in BDNF, the odds of having TBI decreased by 13% (OR: 0.87[95% CI: 0.83-0.91]). BDNF was able to discriminate between TBI cases and non-trauma controls with an AUC of 0.93. BDNF did not discriminate ICH from Non-ICH.

SUMMARY

BDNF levels can discriminate between persons with TBI and those without TBI. As patients with TBI and no intracranial hemorrhage have concussion, decreased BDNF levels may be used to identify persons with significant concussion. This has broad applicability not only in diagnostics as in athletics where BDNF may be used to determine whether a player has had significant concussion (may not return to play immediately) or not (may return to play immediately) but also for return to work. Furthermore, BDNF, its variants or receptors may be used therapeutically in the treatment of TBI.

Example 3: Combination of Serum Glial Fibrillary Acidic Protein (GFAP) and Brain Derived Neurotrophic Factor (BDNF) Concentrations Obtained at Presentation Yields Improved Prediction of Short and Long-Term Post-Concussive Symptoms and Disability Materials and Methods Study Design.
Prospective cohort study.
Study Population: TBI Cases:
Cases were consecutive adult patients (18 years or older) presenting to the Johns Hopkins Hospital Emergency Department (ED) with blunt trauma to the head that occurred within 24 hours of arrival, who had a head computerized tomography CT scan that demonstrated acute traumatic intracranial hemorrhage, and who additionally, had excess serum specimen available in the clinical chemistry laboratory. Patients were excluded if they had a prior surgical procedure on the brain or a brain tumor.

TBI Controls:

TBI Controls were consecutive adult patients (18 years or older) who presented to the ED within 5 days of cases, for blunt head trauma significant enough to warrant receiving a head CT scan as part of their ED evaluation and was interpreted as negative for intracranial hemorrhage. Furthermore, patients were included as controls if they had excess serum specimen available in the clinical chemistry laboratory.

Timing of Blood Draw.

Serum samples were obtained at Emergency Department presentation.

Biomarker Assays.

High sensitivity ELISA assays, developed in Dr. Everett's laboratory for GFAP (glial fibrillary acidic protein) and BDNF (brain derived neurotrophic factor), were used. Protein standards for GFAP and BDNF were from commercial sources.

30 Day Outcomes.

30 day outcomes were ascertained by a review of the Johns Hopkins Hospital electronic medical records. Based on a review of clinical documentation, it was determined whether post-concussive symptoms were present or not. Additionally, disability was assessed based on the Extended Glasgow Outcome Scale (GOSE) (1=no disability, 4 or greater=inability to return to work, 8=death,).

Results

The current diagnostic paradigm of head CT scan only predicts 47.6% of patients with post-concussive symptoms (see table below), whereas a strategy of head CT scan in only those with positive GFAP and/or BDNF predicts post-concussive symptoms in 88.2% of patients with these symptoms, and avoids CT scans in 8/39 subjects (Table 3). The diagnostic accuracy for predicting disability is presented in Table 4 and was equivalent to head CT.

SUMMARY

GFAP and BNDF individually and jointly and their variants (including protein splice variants [isoforms], polymorphisms, and degraded and other post-translational modifications including, but not limited to, citrullination, phosphorylation, acetylation, methylation, etc., as well, BDNF receptors, BDNF pro-hormone and active forms), predict short and long-term post-concussive symptoms and disability after TBI.

Example 4: Serum Brain Derived Neurotrophic Factor (BDNF) Differentiates Between Patients with and without Traumatic Brain Injury Objective diagnosis of traumatic brain injury (TBI) remains challenging. Presently, there are no diagnostic tests that reliably distinguish between persons with TBI and those without. This Example 4 is a follow up to Example 2 above, with the objective being to determine whether brain derived neurotrophic factor (BDNF) values can distinguish between TBI cases and non-trauma controls. As described below, we measured BDNF in serum samples obtained at presentation from patients presenting to an emergency department (ED) within 24 hours of blunt head injury, who met the American College of Emergency Physicians' criteria for obtaining a head CT in head injury (TBI cases), and in ED patients without recent trauma who were evaluated for suspected acute coronary syndrome and ultimately discharged with a non-cardiac diagnosis (non-TBI controls). BDNF was measured using an ELISA assay.

We studied 76 TBI cases and 150 non-TBI controls. TBI cases presented after a fall (34.2%), motor vehicle collision (27.6%), assault (25.0%), pedestrian struck (5.3%), struck by/against an object (4%) or other trauma (4%). BDNF levels were significantly higher in non-TBI controls than TBI cases (median 60.3 [IQR: 41.1-78.2] and 17.5 [IQR: 11.3-29.6] ng/ml, p<0.01 respectively). BDNF discriminates between TBI cases and non-TBI controls with an AUC of

TABLE 3

Prediction of Persistent Post-Concussive Symptoms

|  | Sensitivity | Specificity | Positive predictive value | Negative predictive value |
| --- | --- | --- | --- | --- |
| GFAP | 35.3% (6/17) | 68.2% (15/22) | 46.2% (6/13) | 57.7% (15/26) |
| BDNF | 88.2% (15/17) | 27.3% (6/22) | 48.4% (15/31) | 75.0% (6/8) |
| GFAP and/or BNDF | 88.2% (15/17) | 9.1% (2/22) | 42.9% (15/35) | 50.0% (2/4) |
| Head CT scan | 47.6% (10/21) | 87.5% (21/24) | 76.9% (10/13) | 65.6% (21/32) |

See Table 1 for cut-off

TABLE 4

Prediction of Disability (GOSE of 4 or greater)

|  | Sensitivity | Specificity | Positive predictive value | Negative predictive value |
| --- | --- | --- | --- | --- |
| GFAP | 84.6% (11/13) | 76.5% (26/34) | 57.9% (11/19) | 92.9% (26/28) |
| BDNF | 76.9% (10/13) | 23.5% (8/34) | 27.8% (10/36) | 72.7% (8/11) |
| GFAP and/or BNDF | 84.6% (11/13) | 11.8% (4/34) | 26.8% (11/41) | 66.7% (4/6) |
| Head CT scan | 85.7% (12/14) | 86.5% (32/37) | 70.6% (12/17) | 94.1% (32/37) |

See Table 1 for cut-off 0.94 (95% CI: 0.89-0.96). BDNF did not vary significantly according to TBI severity. Thus, serum BDNF discriminates between TBI cases and non-trauma controls with excellent diagnostic accuracy and may be a candidate biomarker for objective diagnosis of TBI.

Introduction

Detection of mild traumatic brain injury (mTBI) represents a unique clinical challenge with major public health implications. Traumatic brain injury (TBI) is a "silent epidemic" affecting 1.7 million cases each year, and numerous unknown cases who do not seek medical attention. About 75% of TBI cases are classified as mild traumatic brain injury (mTBI), although they can suffer from important neurologic impairment and disabilities. Objective diagnoses of TBI and especially mTBI remain challenging. At present, there is no reliable diagnostic test to distinguish between patients with TBI and those without TBI. For athletes, military personnel and other persons suspected of sustaining mTBI, the current diagnostic paradigm is based on subjective patient report of symptoms and physical exam findings. As a result, there is an unmet clinical need for a novel diagnostic test that can objectively discriminate TBI among undifferentiated blunt head injury patients. Objective detection of TBI may be useful in determining which suspected TBI patients need further diagnostic testing and imaging; acute stage triaging of sport-related TBI and the development of "return to play" guidelines; and identifying military personnel at risk for TBI sequelae.

Brian derived neurotrophic factor (BDNF) is a member of the family of neutrophin proteins that promote the development, maintenance, synaptic plasticity, survival and regeneration of neurons. It is the most abundantly expressed neutrophin in the mature central nervous system. BDNF has been implicated in reducing secondary injury, providing neuroprotection and restoring connectivity in TBI. Prior studies of experimental TBI in rat models have demonstrated that decreases in the expression of BDNF, confers vulnerability to neurons post-trauma. To our knowledge, no studies have examined BDNF values during the acute phase of TBI in humans. We conducted a study to estimate the diagnostic accuracy of BDNF in the distinguishing TBI cases from non-trauma controls.

Materials and Methods

A case-control study of TBI cases and non-trauma controls was conducted after institutional review board approval. The study was conducted at an urban ED that sees 65,000 patients yearly and is part of a 1,000 bed academic, tertiary care institution.

Selection of Subjects.

Patients presenting to an urban academic emergency department (ED) after experiencing blunt head trauma were considered eligible for inclusion as cases if they met the following criteria: presented within 24 hours of injury; met the American College of Emergency Physicians (ACEP) criteria for obtaining head CT scans in TBI; received a non-contrast head CT scan as part of their clinical evaluation; and had excess serum samples available in the clinical chemistry lab. Eligible cases were excluded if they had one of the following prior medical conditions: demyelinating disease; neurodegenerative disease; dementia; stroke; brain tumor; intracranial surgery; or active cancer. Control subjects were selected from an ongoing prospective cohort of ED patients evaluated for suspected acute coronary syndrome. Patients included as control subjects met all of the following criteria: no recent blunt head trauma; deemed to have a non-cardiac condition and discharged home from the ED; had a GCS of 15. Eligible control subjects were excluded if they met any of the exclusion criteria for cases (see above). We also measured BDNF values in blood samples obtained from the Transforming Research and Clinical Knowledge in Traumatic Brain Injury (TRACK-TBI) study.

Data and Blood Sample Collection.

Demographic and clinical data for TBI cases were abstracted from their electronic medical records by clinicians who were blinded to BDNF values. Excess serum samples drawn from TBI cases at ED presentation and stored in a 4° freezer, were obtained from the clinical chemistry laboratory within 1 week of presentation and stored in a −80° F. freezer. Demographic and clinical data for control subjects were collected by trained research assistants who interviewed subjects. Serum samples for non-TBI control subjects were collected during ED visit, processed and stored in a −80° F. freezer. Head CT scans images were read by a board certified neuroradiologist and classified according to the Marshall head CT scan classification scheme.

Measurement of BDNF.

BDNF was measured in batches. Technologist measuring BDNF was blinded to the classification of samples as cases or controls.

Statistical Analyses.

Descriptive statistics were used as to summarize data. Categorical variables (clinical and demographic data) were summarized as proportions. Differences between proportions were assessed with $\chi^2$ tests. Continuous variables (age and BDNF) were summarized using medians and interquartile ranges (IQR). We tested the null hypothesis that the distribution of BDNF values among cases and controls are the same, using the Kruskal-Wallis test. We measured quantified the discriminative ability of BDNF for distinguishing between cases and controls using Area under the Receiver Operator Curve (AUC). To understand the determinants of BDNF in the control population, we constructed univariable and multivariable linear regression models. Variables included in the models (age, gender, race, blood pressure, history of hypertension, history of depression or schizophrenia) were selected based on an apriori literature review. See Fidalgo et al., 30(1) J. ECT 47-61 (2014); Nieto et al., 4 FRONT. PSYCHIATRY Article 45 (2013); Golden et al., 5 PLoS ONE e10099 (2010); and Lommatzsch et al., 26 NEUROBIOL. AGING 115-23 (2005). A two-tailed p-value of <0.05 was considered statistically significant. Statistical analyses were performed using STATA/MP statistical software version 11.2 (StataCorp, College Station, Tex.), and RStudio statistical software version 0.97.312.

Sensitivity Analyses.

We conducted a number of analyses to determine whether our results were influenced by our definition of cases. Our initial definition of cases included subjects who with blunt head injury who met the ACEP criteria for receiving a head CT. In these sensitivity analyses cases were re-defined as subjects who met the definition of TBI proposed by The Demographics and Clinical Assessment Working Group of the International and Interagency Initiative toward Common Data Elements for Research on Traumatic Brain Injury and Psychological Health. Using this definition, there were a number of subjects who met the ACEP criteria for receiving a head CT, but did not meet the TBI definition.

Results

Discriminating Between TBI Cases and Non-TBI Controls.

Figure 11:
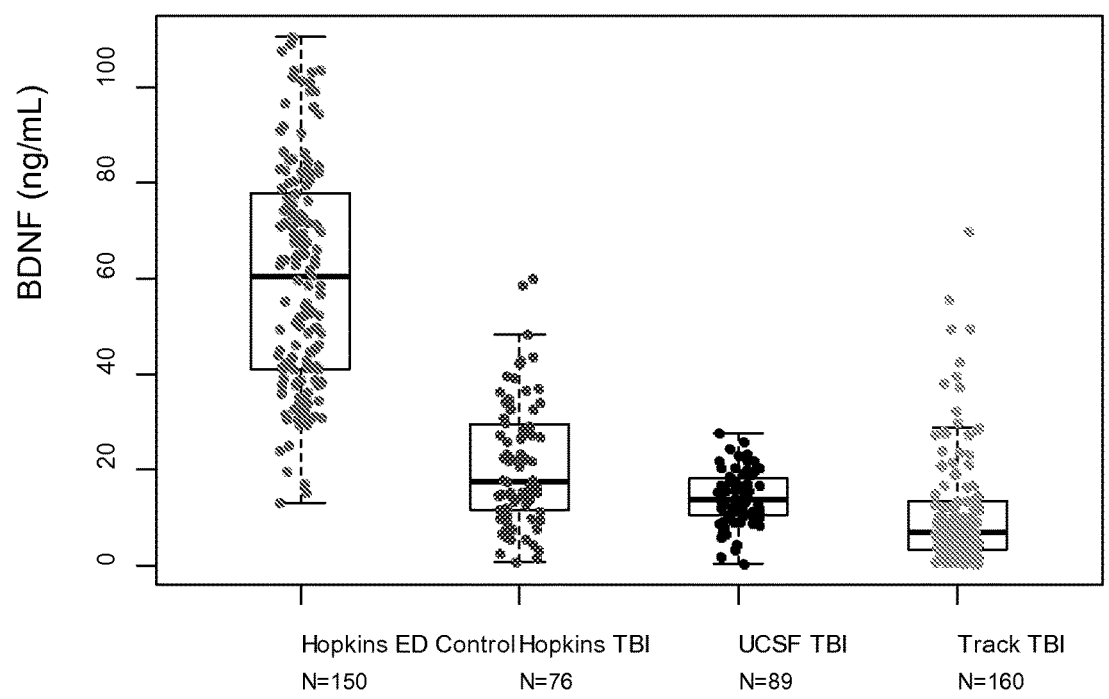
FIG. 11: Distribution of BDNF in TBI cases and non-TBI controls.
Figure 12:
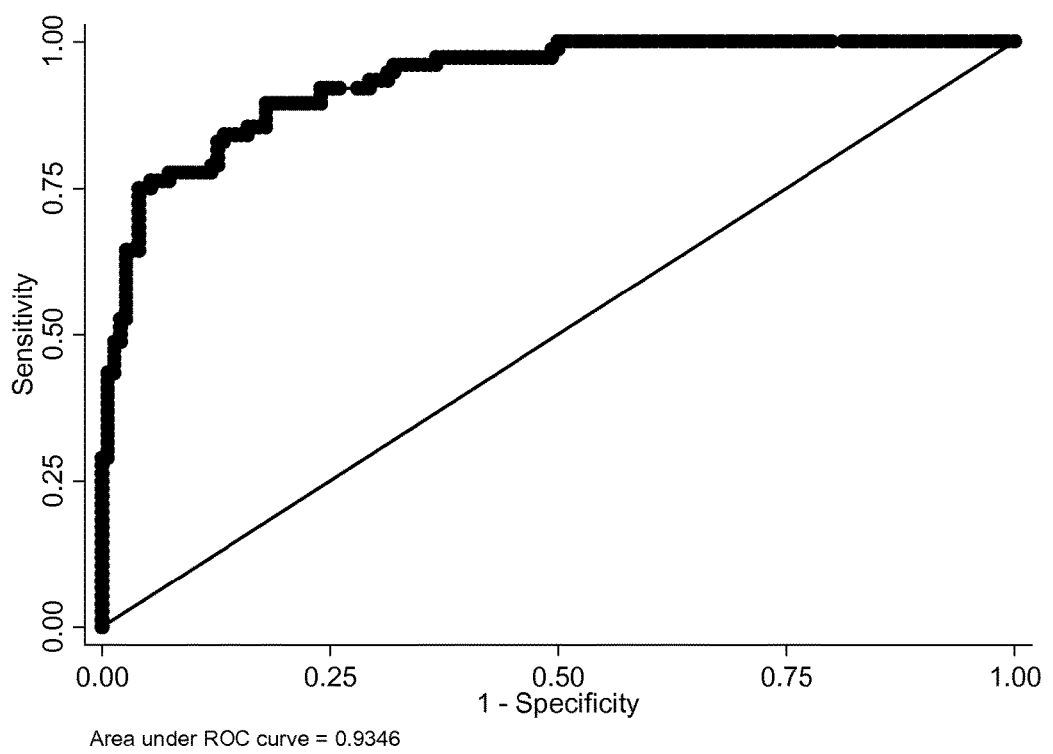
FIG. 12: Discriminative ability of BDNF for distinguishing between TBI cases and Non-TBI controls.
Figure 13:
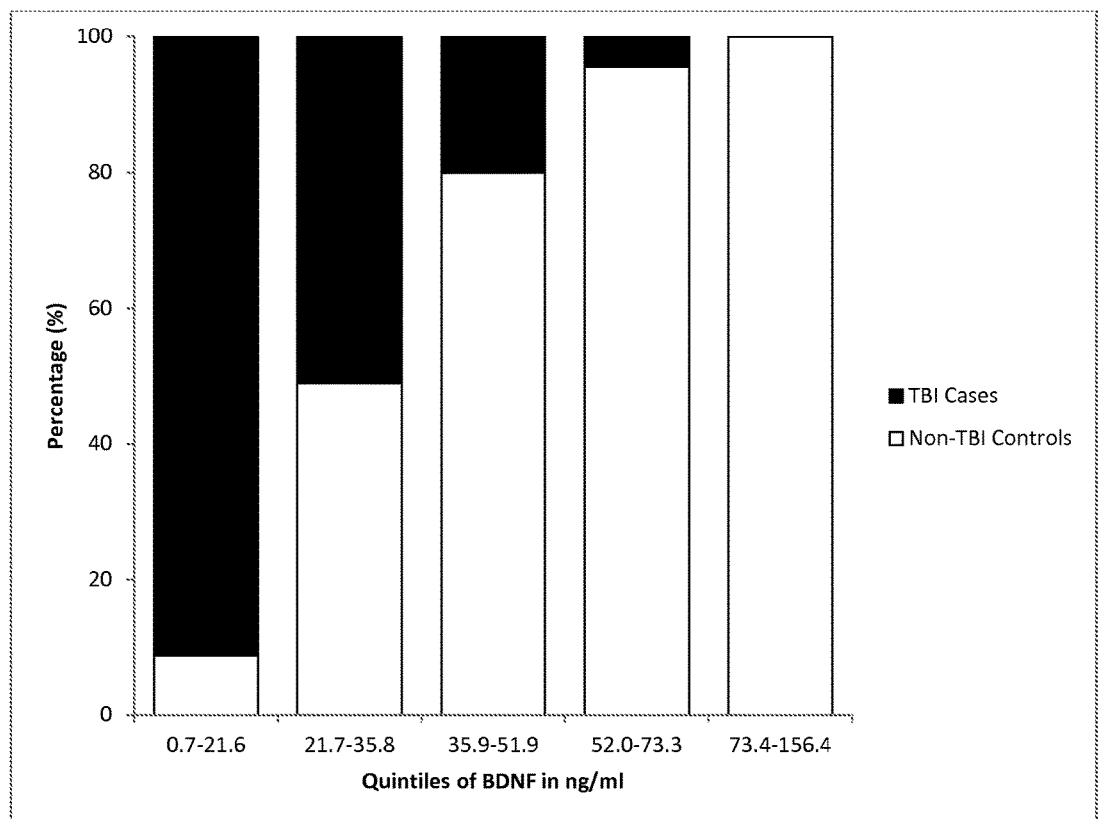
FIG. 13: Distribution of TBI cases and non-TBI controls according to BDNF quintiles.
Figure 14:
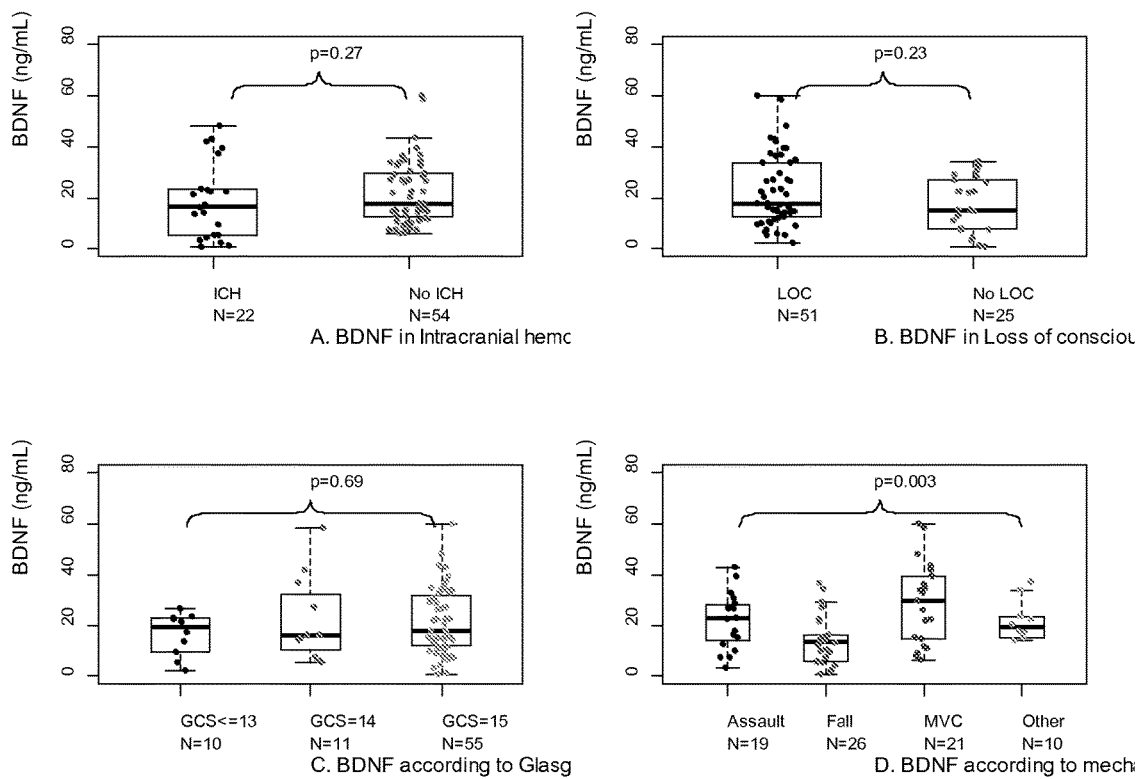
FIG. 14: Distribution of BDNF values according to clinical characteristics of TBI cases.
Figure 15:
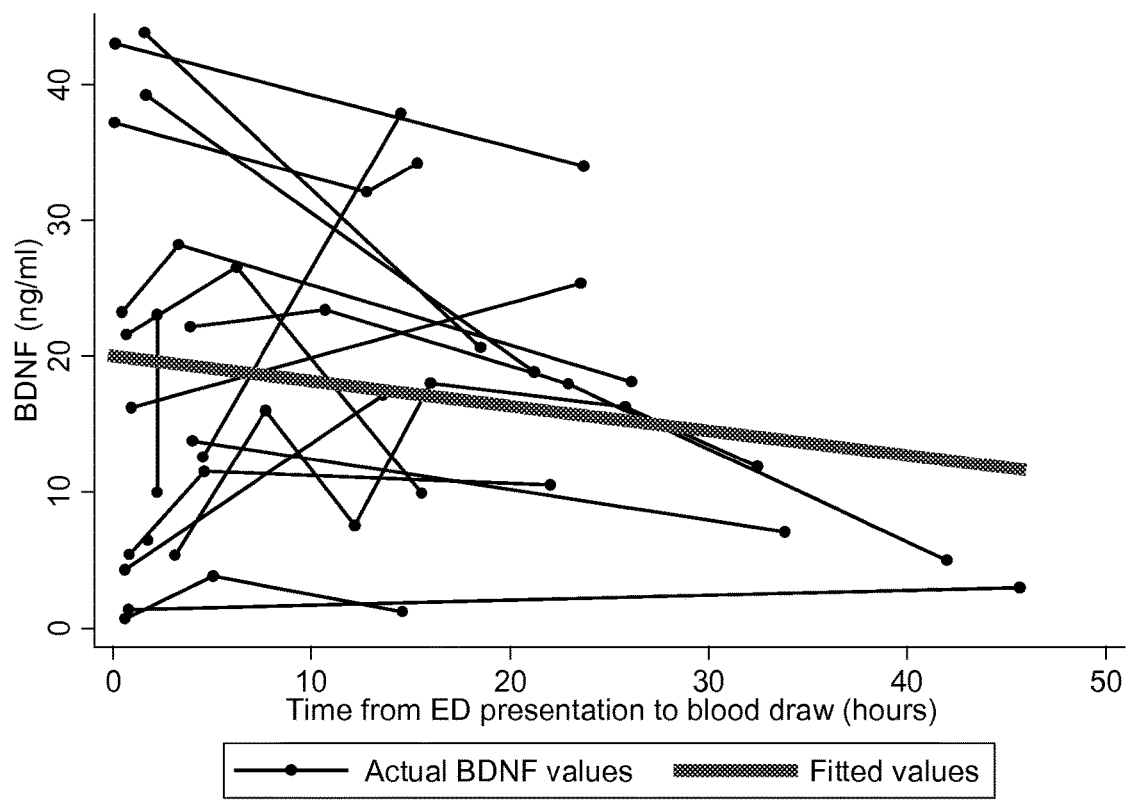
FIG. 15: Serial BDNF values in 18 TBI patients with repeat measurements within 48 hours of presentation.
Figure 16:
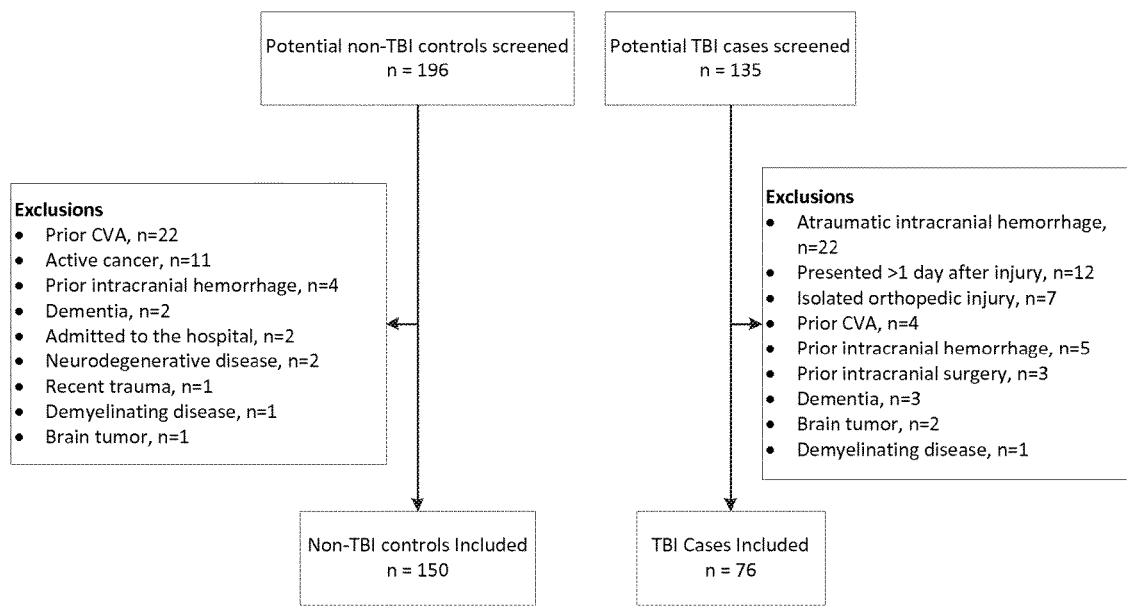
FIG. 16: Derivation of study population.

We studied 76 TBI cases meeting the ACEP criteria for receiving a head CT, who presented between November 2012 and September 2013. Additionally, we also studied 150 non-TBI control subjects presenting between January 2012 and February 2013 (supplemental FIG. 1). Non TBI-controls subjects were older, and had more females and African-Americans than cases (Table 5). Majority of TBI cases either presented after a fall (34.2%), motor vehicle collision (27.6%) or assault (25.0%) (Table 5). The median time between ED arrival and serum samples draws for TBI cases was 1.8 hours (IQR: 0.9-2.9 hours). BDNF levels were significantly higher in non-TBI controls (median 60.3 [IQR: 41.1-78.2] ng/ml) than in TBI cases (median 17.5 [IQR: 11.3-29.6] ng/ml), p<0.01. BDNF values did not vary significantly according to severity of TBI (FIG. 11). BDNF discriminates between TBI cases and non-TBI controls with an AUC of 0.94 (95% CI: 0.89-0.96) (FIG. 12). Almost all subjects (91.3%) in the lowest quintile of BDNF were TBI cases. Similarly, all subjects in the highest quintile of BDNF were non-TBI controls (FIG. 13). Using a cutoff of the upper limit of the second quintile (35.9 ng/ml), the sensitivity, specificity, positive predictive value and negative predictive value for detecting TBI are: 85.5%, 82.7%, 71.4%, 91.9% respectively.

TABLE 5

Demographic and Clinical Characteristics of Study Population

| | Controls n = 150 | Cases n = 76 | p Value |
|---|---|---|---|
| Median Age in years (IQR) | 54 (47-62) | 47 (30-56) | <0.01 |
| Female (%) | 79 (52.7) | 29 (38.2) | 0.04 |
| Race (%) | | | <0.01 |
| African-American | 116 (77.3) | 41 (54.0) | |
| White | 30 (20.0) | 25 (32.9) | |
| Other | 4 (2.7) | 10 (13.2) | |
| Mechanism of Injury (%) | | | <0.01 |
| No trauma | 150 (100) | 0 (0) | |
| Fall | 0 (0) | 26 (34.1) | |
| MVC | 0 (0) | 21 (27.6) | |
| Assault | 0 (0) | 19 (25.0) | |
| Pedestrian struck | 0 (0) | 4 (5.3) | |
| Struck by/against | 0 (0) | 3 (4.0) | |
| Other trauma | 0 (0) | 3 (4.0) | |
| Glasgow Outcome Scale (%) | | | <0.01 |
| 3-8 | 0 (0) | 5 (6.6) | |
| 9-12 | 0 (0) | 3 (5.0) | |
| 13 | 0 (0) | 2 (2.6) | |
| 14 | 0 (0) | 11 (14.5) | |
| 15 | 150 (100) | 55 (72.4) | |
| Marshall head CT Classification >1 | NA | 24 (31.6) | |

Sixty-one TBI cases met the Common Data Elements definition for TBI.[22] BDNF values were lower among these TBI cases than non-TBI controls (median 17.8 [95% CI: 10.2-31.8] vs 60.3 [95% CI: 41.1-78.2] ng/ml respectively). BDNF discriminated these TBI cases from non-TBI controls with an AUC of 0.93 (95% CI: 0.88-0.96).

Predictors of BDNF Values in Non-TBI Control Subjects.

Among non-TBI controls, median BDNF levels were greater in females than in males (69.1 [IQR: 41.4-82.4] vs 52.7 [IQR: 38.7-71.8] ng/ml respectively). Similarly, among non-TBI controls, BDNF values increased with increasing mean arterial pressure (2.8 ng/ml increase per 10 mmHg increase in mean arterial pressure). After adjusting for age, gender, race, hypertension, diabetes, history of psychiatric illness and mean arterial pressure, only gender and mean arterial pressure remained independent predictors of BDNF among non-TBI controls (Table 6).

TABLE 6

Determinants of BDNF in the control population (n = 150)

| | Unadjusted regression co-efficient (95% CI) | Adjusted regression co-efficient (95% CI) |
|---|---|---|
| Age per decile (years) | −0.9 (−4.5 to 2.7) | −1.7 (−5.3 to 2.0) |
| Gender | | |
| Female | Reference | Reference |
| Male | −7.2 (−15.4 to 1.0) | −8.8 (−17.0 to −0.6) |
| Race | | |
| African-American | Reference | Reference |
| Caucasian | −9.6 (−19.8 to 0.7) | −8.8 (−18.8 to 1.3) |
| Other | 0.2 (−25.3 to 25.7) | 0.6 (−24.8 to 26.0) |
| Mean arterial pressure per 10 mmHg | 2.8 (0.7 to 4.9) | 3.0 (0.9 to 5.1) |
| History of hypertension | −0.0 (−9.1 to 9.0) | −0.3 (−9.7 to 9.1) |
| History of depression or schizophrenia | −1.2 (−12.7 to 10.2) | −3.3 (−14.6 to 8.0) |

Stability of BDNF.

As TBI case and non-TBI control samples were collected differently, we determined the stability of BDNF at room temperature (RT) and 4° C. over 48 hours. Storage conditions had little effect on BDNF stability. Therefore BDNF is very stable in plasma with a minimal loss of detection when stored for 12-48 hours before freezing.

Figure 17:
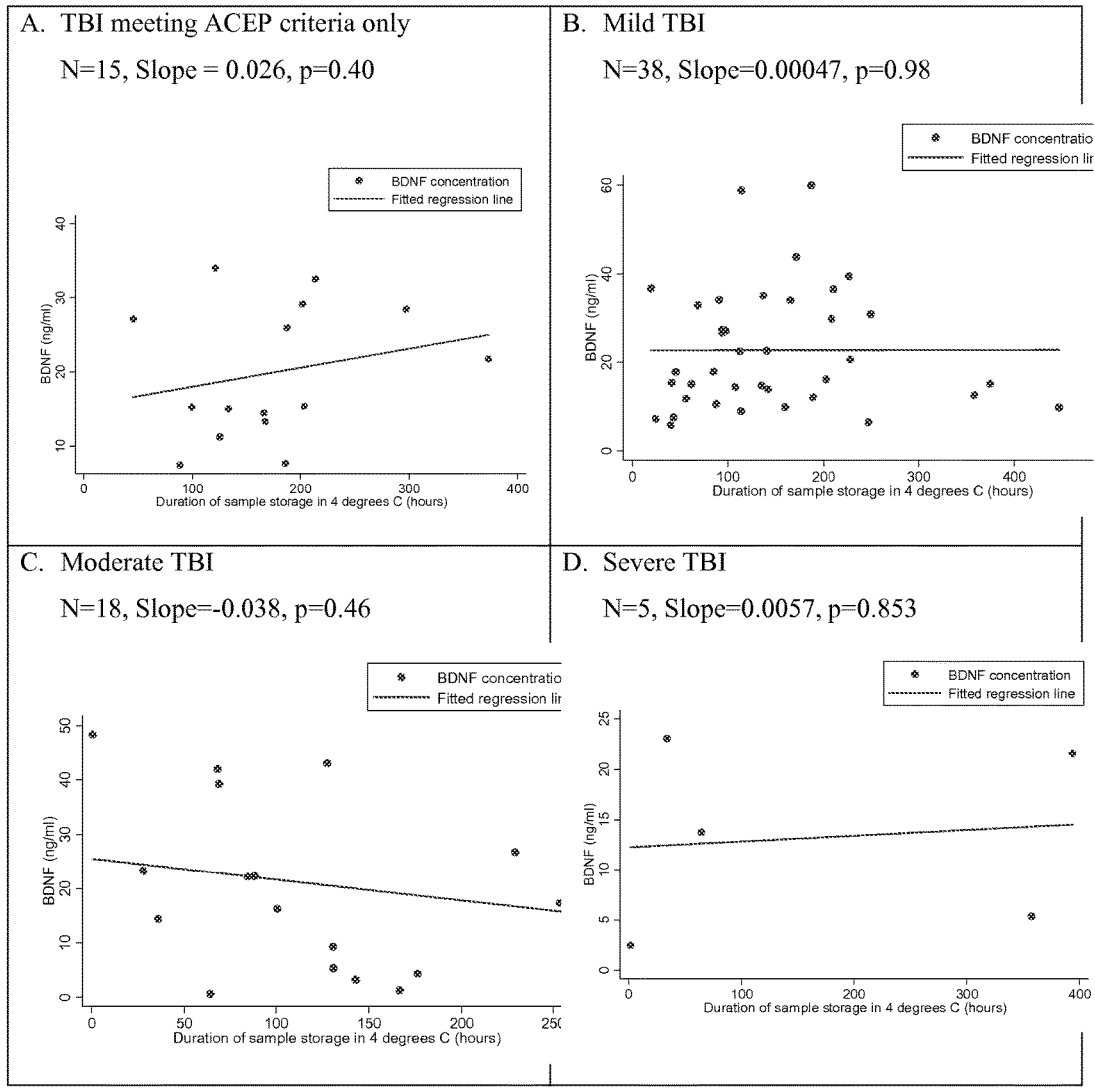
FIG. 17: Association between duration of sample storage in 4° C. and BDNF concentration according to TBI category.
Figure 18:
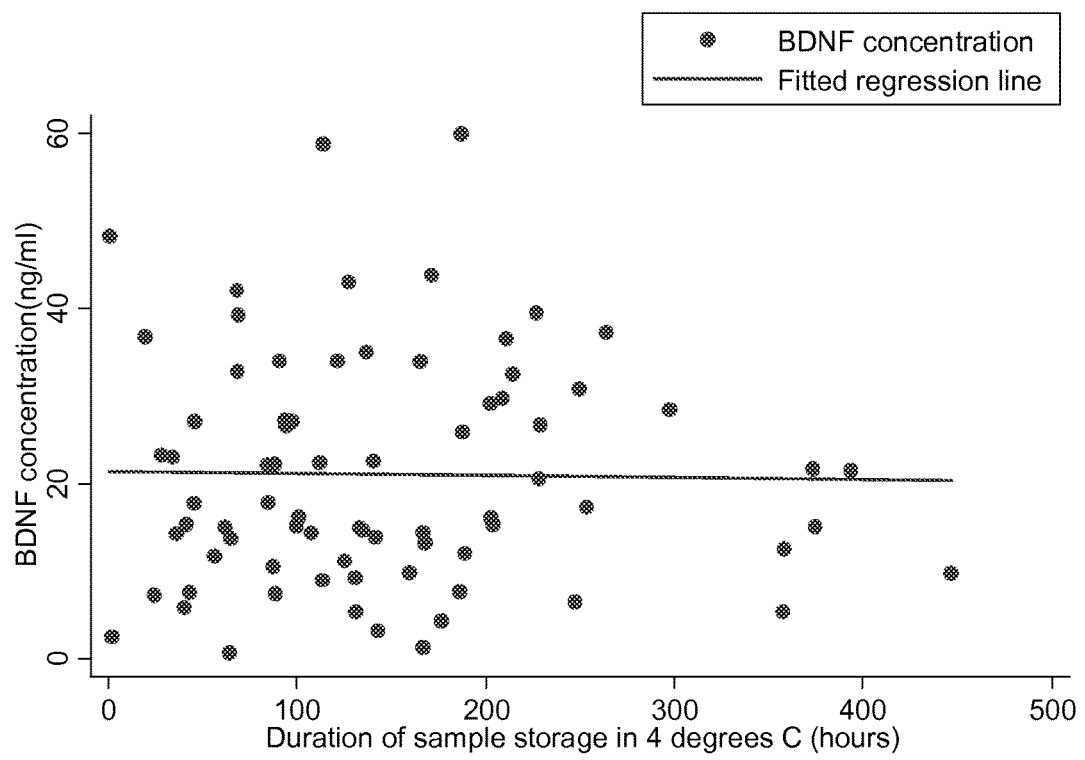
FIG. 18: Association duration of sample storage in 4° C. and BDNF concentration for all TBI cases.

Among TBI samples, there was no statistically significant association between duration of sample storage in 4° C. and BDNF levels (FIGS. 17-18). After excluding TBI cases that were stored in 4° C. for more than 48 hours, the median BDNF value remained significantly lower in TBI cases than controls (16.6 [IQR: 7.3-26.1] vs 60.3 [IQR: 41.1-78.2], p<0.01).

Discussion

To our knowledge, this is the first report of the diagnostic accuracy of circulating BDNF for discriminating between human TBI cases and non-TBI controls. BDNF is an appealing candidate biomarker for detecting TBI for numerous reasons. First, our study results demonstrate a very strong association between BDNF and TBI, yielding an excellent discriminative ability of 0.94 (as measured by the c-statistic). Secondly, BDNF is the most abundantly expressed neutrophin and can be readily and reliably measured in serum. Additionally, our data demonstrates that BDNF is stable and has low analytical variation, increasing the likelihood for reliable results in clinical and austere environments. Thirdly, BDNF expression is predominantly in brain and spinal cord tissue, limiting the likelihood for false positive results in multi-system trauma cases.

In our study, although control subjects with a history of a psychiatric disorder had lower median BDNF values than those without a history of a psychiatric disorder, this difference was not statistically significant. Additionally, after adjusting for age, gender, race, hypertension, diabetes and mean arterial pressure, history of psychiatric disorder was not an independent predictor of BDNF levels. However, mean arterial pressure and gender were found to be independent predictors of BDNF in control subjects. It is unclear whether these associations hold true in TBI patients. However, our findings regarding gender suggest that gender-specific cut-offs may be important in determining the reference values of BDNF.

CONCLUSION

Serum BDNF discriminates between TBI cases and non-trauma controls with excellent diagnostic accuracy and may be a candidate biomarker for objective diagnosis of TBI.

We claim:

1. A method of detecting protein biomarkers in a sample obtained from a patient having or at risk of having traumatic brain injury (TBI) and/or intracerebral hemorrhage (ICH), the method comprising:

detecting brain derived neurotrophic factor (BDNF), glial fibrillary acidic protein (GFAP), neuron specific enolase (NSE) and metallothionein 3 (MT3) protein biomarkers in a biological sample obtained from the patient by contacting the sample with detectable binding agents that specifically bind to the biomarkers and detecting specific binding between the specific binding agents and the biomarkers using a detection assay comprising biomarker controls.

2. The method of claim 1, wherein the sample is obtained from a patient having or at risk of having short or long-term post-concussive symptoms or disability after TBI.

3. The method of claim 1, wherein the sample is obtained from a patient having traumatic brain injury (TBI) and requiring central nervous system (CNS) imaging for risk of CNS damage.

4. The method of claim 1, wherein the biological sample is selected from the group consisting of blood, plasma, serum or cerebrospinal fluid (CSF).

5. The method of claim 1, wherein at least one of the protein biomarkers is methylated, citrullinated, glycosylated, acetylated, or phosphorylated.

6. The method of claim 1, wherein the detection assay is an enzyme linked immunosorbent assay (ELISA), a chemiluminescence-based immunoassay, a fluorescence-based immunoassay, or mass spectrometry.

7. The method of claim 1, further comprising detecting in the sample one or more protein biomarkers selected from neurogranin (NRGN); myelin basic protein (MBP); S100B; intercellular adhesion molecule-5 (ICAM5); tubulin beta-4B chain; tubulin alpha-1B chain; 2',3'-cyclic nucleotide 3'-phosphodiesterase (CNPase); peptidylprolyl isomerase A (PPIA), Septin-7; Elongation factor1-alpha2; tubulin polymerization promoting protein (TPPP); tubulin polymerization promoting protein family member 3 (TPPP3); oligodendrocyte-specific cytoskeletal protein (Ermin); Ermin Isoform 2; N-myc downstream-regulated gene 2 protein Isoform 2 (NDRG2 Isoform 2); astrotactin 1 (ASTN1); brain angiogenesis inhibitor 3 (BAI3); carnosine dipeptidase 1 (CNDP1); glutamate receptor metabotropic 3 (GRM3); kelch-like protein 32 (KLH32); melanoma antigen family E,2 (MAGE2); neuregulin 3 (NRG3); oligodendrocyte myelin glycoprotein (OMG); solute carrier family 39 (zinc transporter); reticulon 1 (RTN1); or peptidylarginine deiminase (types 1-4 and 6) (PADI1-PADI4 and PADI6).

* * * * *